United States Patent
Potyrailo et al.

(10) Patent No.: US 12,306,127 B2
(45) Date of Patent: May 20, 2025

(54) SYSTEM AND METHOD FOR MULTI-GAS SENSING AT A SINGLE OPERATING TEMPERATURE

(71) Applicant: General Electric Company, Schenectady, NY (US)

(72) Inventors: Radislav Alexandrovich Potyrailo, Niskayuna, NY (US); Janell Marie Crowder, Clifton Park, NY (US)

(73) Assignee: GE Infrastructure Technology LLC, Greenville, SC (US)

( * ) Notice: Subject to any disclaimer, the term of this patent is extended or adjusted under 35 U.S.C. 154(b) by 296 days.

(21) Appl. No.: 17/859,874

(22) Filed: Jul. 7, 2022

(65) Prior Publication Data

US 2024/0011928 A1    Jan. 11, 2024

(51) Int. Cl.
  *G01N 27/22*    (2006.01)
  *G01N 1/44*    (2006.01)
  (Continued)

(52) U.S. Cl.
  CPC .............. *G01N 27/221* (2013.01); *G01N 1/44* (2013.01); *G01N 33/0016* (2013.01);
  (Continued)

(58) Field of Classification Search
  CPC .... G01N 27/221; G01N 1/44; G01N 33/0016; G01N 33/0027; G01N 33/0031; H05B 3/02
  See application file for complete search history.

(56) References Cited

U.S. PATENT DOCUMENTS

| | | |
|---|---|---|
| 4,457,161 A | 7/1984 | Iwanaga et al. |
| 5,320,814 A | 6/1994 | Walt et al. |
| | (Continued) | |

FOREIGN PATENT DOCUMENTS

WO    2011008043 A3    1/2011

OTHER PUBLICATIONS

Jeong et al., "Rational Design of Semiconductor-Based Chemiresistors and their Libraries for Next-Generation Artificial Olfaction," Advanced Materials, Sep. 15, 2020, 47 Pages.
(Continued)

*Primary Examiner* — Ryan D Walsh
(74) *Attorney, Agent, or Firm* — Fletcher Yoder, P.C.

(57) ABSTRACT

A system and a method for multi-gas sensing using dielectric excitation of a single sensing material operated at a single operating temperature. Contrary to conventional gas sensor designs, embodiments of the gas sensors disclosed herein implement a metal oxide semiconductor sensing material maintained at a constant temperature, wherein dielectric excitation responses of the sensing material are measured at this constant temperature while the sensing material is exposed to a fluid sample. The disclosed gas sensors and gas sensing methods unexpectedly provide desirable characteristics, such as enhanced multi-gas differentiation, while operating at the constant operating temperature. For example, by measuring dielectric excitation responses of using at least one gas sensing element at a single operating temperature, the disclosed gas sensors and gas sensing methods demonstrate superior multi-gas differentiation compared to other gas sensors and other gas sensing methods that rely on multiple resistance measurements performed at several different operating temperatures.

17 Claims, 19 Drawing Sheets

(51) Int. Cl.
　　　*G01N 33/00*　　　(2006.01)
　　　*H05B 3/02*　　　(2006.01)
(52) U.S. Cl.
　　　CPC ..... *G01N 33/0027* (2013.01); *G01N 33/0031* (2013.01); *H05B 3/02* (2013.01)

(56) References Cited

U.S. PATENT DOCUMENTS

| | | | |
|---|---|---|---|
| 5,345,213 | A | 9/1994 | Semancik et al. |
| 6,010,616 | A | 1/2000 | Lewis et al. |
| 6,095,681 | A | 8/2000 | Kunt et al. |
| 7,329,389 | B2 | 2/2008 | Horovitz et al. |
| 7,849,727 | B2 | 12/2010 | Gardner et al. |
| 9,312,713 | B2 | 4/2016 | Graf et al. |
| 9,618,491 | B1 | 4/2017 | Kellaway et al. |
| 9,995,593 | B2 | 6/2018 | Badeja et al. |
| 2002/0092525 | A1 | 7/2002 | Rump et al. |
| 2002/0121440 | A1* | 9/2002 | Morris ............... G01N 33/0031 422/98 |
| 2013/0115706 | A1 | 5/2013 | Gouma |
| 2016/0187277 | A1* | 6/2016 | Potyrailo ............. G01N 27/026 324/633 |
| 2016/0187279 | A1 | 6/2016 | Tayebi et al. |
| 2018/0231485 | A1* | 8/2018 | Potyrailo ........... G01N 33/0047 |
| 2020/0386701 | A1* | 12/2020 | Potyrailo ............. G01N 27/122 |
| 2020/0386728 | A1 | 12/2020 | Potyrailo |
| 2020/0400635 | A1 | 12/2020 | Potyrailo et al. |
| 2021/0072175 | A1 | 3/2021 | Potyrailo et al. |
| 2021/0109049 | A1 | 4/2021 | Potyrailo |
| 2021/0278384 | A1* | 9/2021 | Potyrailo ........... G01N 33/0031 |
| 2024/0011900 | A1* | 1/2024 | Potyrailo ........... G01N 33/0006 |
| 2024/0011930 | A1* | 1/2024 | Potyrailo ............ G01N 27/223 |
| 2024/0011934 | A1* | 1/2024 | Potyrailo ............ G01N 27/404 |
| 2024/0011962 | A1* | 1/2024 | Potyrailo ........... G01N 33/0016 |
| 2024/0013647 | A1* | 1/2024 | Potyrailo ........... G01N 27/4163 |

OTHER PUBLICATIONS

Persaud et al., "Analysis of discrimination mechanisms in the mammalian olfactory system using a model nose," Nature vol. 299, Sep. 23, 1982, pp. 352-355.

Hikita et al., "New Gas-Sensing Method for Detecting Carbon Monoxide by Use of the Complex Impedance of a CuO/ZnO Heterocontact under a dc Bias Voltage," Tokyo, Japan, vol. 77, No. 7, Sep. 10, 1993, pp. 1961-1964.

Weimar et al., "AC Measurements on Tin Oxide Sensors to Improve Selectivities and Sensitivities," Sensors and Actuators B 26-27, 1995, pp. 13-18.

Potyrailo et al., "Extraordinary performance of semiconducting metal oxide gas sensors using dielectric excitation," Nature Electronics, 2020, https://doi.org/10.1038/s41928-020-0402-3 , 59 Pages.

Gopel et al., "SnO2 sensors: current status and future prospects," Sensors and Actuators, Institute of Physical and Theoretical Chemistry and Centre of Inteiface Analysis and Sensors, B26-27, Tubingen, Germany, 1995, pp. 1-12.

Rheaume et al., "A review of recent progress in sensing of gas concentration by impedance change," Jan. 13, 2011, Ionics (2011) 17:99-108, DOI 10.1007/s11581-010-0515-1, pp. 99-108.

Joo et al., "Pattern recognition of gas sensor array using characteristics of impedance," Sensors and Actuators B 77 (2001), School of Electronic & electrical engineering, Kyungpook, South Korea, pp. 209-214.

Schüler et al., "Impedance based detection of HMDSO poisoning in metal oxide gas sensors," Apr. 4, 2017, Technisches Messen 2017, https://doi.org/10.1515/teme-2017-0002 , pp. 697-705.

Nakata et al., "Gas Sensing Based on a Nonlinear Response: Discrimination between Hydrocarbons and Quantification of Individual Components in a Gas Mixture," Analytical Chemistry, vol. 68, No. 13, Jul. 1, 1996, pp. 2067-2072.

Heilig et al., "Gas identification by modulating temperatures of SnO2-based thick film sensors," Dec. 2, 1996, Sensors and Actuators B 43 (1997), Tubingen, Germany, pp. 45-51.

Chakraborty et al., "Selective detection of methane and butane by temperature modulation in iron doped tin oxide sensors," Dec. 13, 2005, Kolkata 700032, India, Sensors and Actuators B 115 (2006), pp. 610-613.

Meier et al., "The potential for and challenges of detecting chemical hazards with temperature-programmed microsensors," Nov. 7, 2006, Gaithersburg, MD 20899-8362, USA, Sensors and Actuators B 121 (2007), pp. 282-294.

Meier et al., "Detecting Chemical Hazards with Temperature-Programmed Microsensors: Overcoming Complex Analytical Problems with Multidimensional Databases" Annual Review of Analytical Chemistry vol. 2, 2009, 24 Pages.

Lee et al., "Temperature modulation in semiconductor gas sensing," Apr. 14, 1999, Sensors and Actuators B 60, School of Applied Science, Unilersity of Tasmania, Tasmania 7250, Australia, pp. 35-42.

Zhang et al., "A novel method in the gas identification by using WO3 gas sensor based on the temperature-programmed technique," Sensors andActuators B 206(2015), http://dx.doi.org/10.1016/j.snb.2014.09.063 , pp. 220-229.

Hossein-Babaei et al., "Recognition of complex odors with a single generic tin oxide gas sensor," Dec. 24, 2013, Sensors and Actuators B 194 (2014), http://dx.doi.org/10.1016/j.snb.2013.12.061 , pp. 156-163.

Hossein-Babaei et al., "A breakthrough in gas diagnosis with a temperature-modulated generic metal oxide gas sensor," Mar. 5, 2012, Sensors and Actuators B 166-167, pp. 419-425.

Huang et al., "Gas sensing behavior of a single tin dioxide sensor under dynamic temperature modulation," Dec. 15, 2003, doi:10.1016/j.snb.2003.12.013 , Sensors and Actuators B 99 (2004), pp. 444-450.

Gutierrez-Osuna et al., "Transient response analysis for temperature-modulated chemoresistors," Sensors and Actuators B 93 (2003), doi:10.1016/S0925-4005(03)00248-X , pp. 57-66.

Kato et al., "Temperature-dependent dynamic response enables the qualification and quantification of gases by a single sensor," Aug. 6, 1996, Sensors and Actuators B 40 (1997), pp. 33-37.

Schütze et al., "Highly Sensitive and Selective VOC Sensor Systems Based on Semiconductor Gas Sensors: How to?," Mar. 1, 2017, Environments 2017, vol. 4, Issue 20, doi:10.3390/environments4010020, 13 Pages.

Schüler et al., "Metal oxide semiconductor gas sensor self-test using Fourier-based impedance spectroscopy," Sep. 25, 2014, Journal of sensors and sensor systems, doi:10.5194/jsss-3-213-2014 , pp. 213-221.

Schüler et al., "A novel approach for detecting HMDSO poisoning of metal oxide gas sensors and improving their stability by temperature cycled operation," Oct. 19, 2015, Journal of Sensors and Sensor Systems, doi:10.5194/isss-4-305-2015 , pp. 305-311.

Wen et al., "A Gas Mixture Prediction Model Based on the Dynamic Response of a Metal-Oxide Sensor," Sep. 11, 2019, micromachines, doi:10.3390/mi10090598 , 11 pages.

Beccherelli et al., "Design of a very large chemical sensor system for mimicking biological olfaction," Nov. 24, 2009, Sensors and Actuators B 146 (2010), doi:10.1016/j.snb.2009.11.031 , pp. 446-452.

Bernabei et al., "Large-Scale Chemical Sensor Array Testing Biological Olfaction Concepts," IEEE Sensors Journal, vol. 12, No. 11, Nov. 2012, pp. 3174-3183.

Marco et al., "A biomimetic approach to machine olfaction, featuring a very large-scale chemical sensor array and embedded neuro-bio-inspired computation," Dec. 21, 2013, Microsyst Technol, DOI 10.1007/s00542-013-2020-8 , 14 Pages.

Ni et al., "Orthogonal gas sensor arrays with intelligent algorithms for early warning of electrical fires," Nov. 17, 2007, Sensors and Actuators B 130 (2008), pp. 889-899.

Lee, "Linear gas sensing with dielectric excitation," May 2020, vol. 3, Nature Electronics, pp. 239-240.

(56) References Cited

OTHER PUBLICATIONS

Ulmer et al., "Sensor arrays with only one or several transducer principles? The advantage of hybrid modular systems," May 6, 1999, Sensors and Actuators B 65 (2000), pp. 79-81.
Hagleitner et al., "Smart single-chip gas sensor microsystem," Nov. 15, 2001, Letters to Nature, vol. 414, pp. 293-296.
Jin et al., "Evaluation of Multitransducer Arrays for the Determination of Organic Vapor Mixtures," Jan. 1, 2008, vol. 80, No. 1, Analytical Chemistry, pp. 227-236.
Jin et al., "Limits of Recognition for Binary and Ternary Vapor Mixtures Determined with Multitransducer Arrays," Oct. 1, 2008, vol. 80, No. 19, Analytical Chemistry, pp. 7283-7293.
Pardo et al., "Data analysis for a hybrid sensor array," Jul. 2, 2004, Sensors and Actuators B 106 (2005), pp. 136-143.
Jin et al., "A Comparison of Multi-Transducer Arrays and Single-Transducer Arrays for the Determination of Multi-Vapor Mixtures," IEEE Sensors 2007 Conference, pp. 1217-1220.
Scholten et al., "Vapor Discrimination with Single- and Multitransducer Arrays of Nanoparticle-Coated Chemiresistors and Resonators," Jun. 2013, vol. 13, No. 6, IEEE Sensors Journal, pp. 2146-2154.
International Search Report and Written Opinion for PCT/US2023/026948 mailed Sep. 12, 2023, 16 pages.

\* cited by examiner

SYSTEM AND METHOD FOR MULTI-GAS SENSING AT A SINGLE OPERATING TEMPERATURE

STATEMENT REGARDING FEDERALLY SPONSORED RESEARCH & DEVELOPMENT

This invention was made with Government support under Agreement No. W15QKN-18-9-1004 awarded by the ACC-NJ to the CWMD Consortium. The Government has certain rights in the invention.

BACKGROUND

The subject matter disclosed herein generally relates to gas sensing, and more specifically relates to gas sensing using metal oxide semiconductor (MOS) sensors.

Metal oxide semiconductor (MOS) sensors can be operated as chemiresistors and are popular because of their ability to detect numerous gases with the proper selection of the base semiconductor material and doping materials. In such gas-responsive chemiresistor, a change in resistance of the MOS sensing element is measured, and this change in resistance is proportional to the gas concentrations in a fluid sample. However, the limited selectivity of MOS gas-responsive chemiresistor has hindered the use of such sensor in certain multi-gas sensing applications. Additionally, to achieve at least some gas selectivity, traditional MOS-based gas sensors require resistance measurements be performed at more than one operation temperature, in particular using at least two different operating temperatures, which can, decrease the longevity of the sensor, and introduce undesirable effects on the electrical measurements.

BRIEF DESCRIPTION

With the foregoing in mind, present embodiments are directed to a system and a method for multi-gas sensing using dielectric excitation of a single sensing material at a single constant operating temperature. Conventional gas sensor designs implement metal oxide semiconductor sensing materials that typically operate at several different operating temperatures while resistance responses are collected in order to differentiate between different gases in a fluid sample. In contrast, for present embodiments, dielectric excitation responses of the sensing material are measured at this constant temperature while the sensing material is exposed to a fluid sample. Present embodiments demonstrate that, when the dielectric excitation response of the gas sensing material is measured at a constant operating temperature, superior multi-gas differentiation is achieved relative to the differentiation achievable based on measuring resistance responses of the same gas sensing material at multiple different operating temperatures. For example, by measuring dielectric excitation responses of using at least one gas sensing element at a single operating temperature, the disclosed gas sensors and gas sensing methods demonstrate superior multi-gas selectivity compared to other gas sensors and other gas sensing methods that rely on multiple resistance measurements performed at several different operating temperatures.

For example, in an embodiment, a gas sensor system for multi-gas analysis of a fluid sample includes a gas sensing element configured to contact the fluid sample, a heating element coupled to the gas sensing element and configured to heat the gas sensing element, and a heating element controller operatively coupled to the heating element and configured to control the heating element to heat the gas sensing element to a constant temperature while the gas sensing element contacts the fluid sample. The gas sensor system includes a measurement circuit operatively coupled to the gas sensing element and configured to provide dielectric excitation to, and to measure dielectric excitation responses of, the gas sensing element while the gas sensing element is heated to the constant temperature and contacts the fluid sample, wherein the dielectric excitation responses provide enhanced differentiation between at least two gases in the fluid sample as compared to resistance responses of the gas sensing element when contacting the fluid sample at multiple operating temperatures.

In an embodiment, a method of operating a gas sensor for multi-gas analysis of a fluid sample includes exposing a gas sensing material of the gas sensor to the fluid sample; controlling, via at least one heating element controller of the gas sensor, a heating element of the gas sensor to heat the gas sensing material to a constant temperature; and measuring, via a measurement circuit of the gas sensor, dielectric excitation responses of the gas sensing material while the gas sensing material is heated to the constant temperature and exposed to the fluid sample. The method includes receiving, via an on-board data processor of the gas sensor, the dielectric excitation responses of the gas sensing material at the constant temperature; and differentiating, via the on-board data processor, at least two gases in the fluid sample based on at least a portion of the received dielectric excitation responses.

In an embodiment, a method of manufacturing a gas sensor for multi-gas analysis includes determining a plurality of analyte gases to be differentiated by the gas sensor. The method may include determining a type of base semiconducting metal oxide to use and dopant or dopants to use for detection of analyte gases to be differentiated by the gas sensor. The method includes determining an operating temperature to operate a gas sensing material of the gas sensor at which the gas sensing material reversibly interacts with each of the plurality of analyte gases, and configuring a first heating element controller and a second heating element controller of the gas sensor to provide a combined voltage to a heating element of the gas sensor to heat the gas sensing material to the constant operating temperature. The method includes determining a plurality of frequencies for the dielectric excitation of the sensor to be applied to the gas sensing material to measure dielectric excitation responses of the gas sensing material as the gas sensing material interacts with the plurality of analyte gases, and configuring a measurement circuit of the gas sensor to apply each of the plurality of frequencies for the dielectric excitation of the gas sensing material to measure the dielectric excitation responses of the gas sensing material as the gas sensing material interacts with the plurality of analyte gases at the operating temperature.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
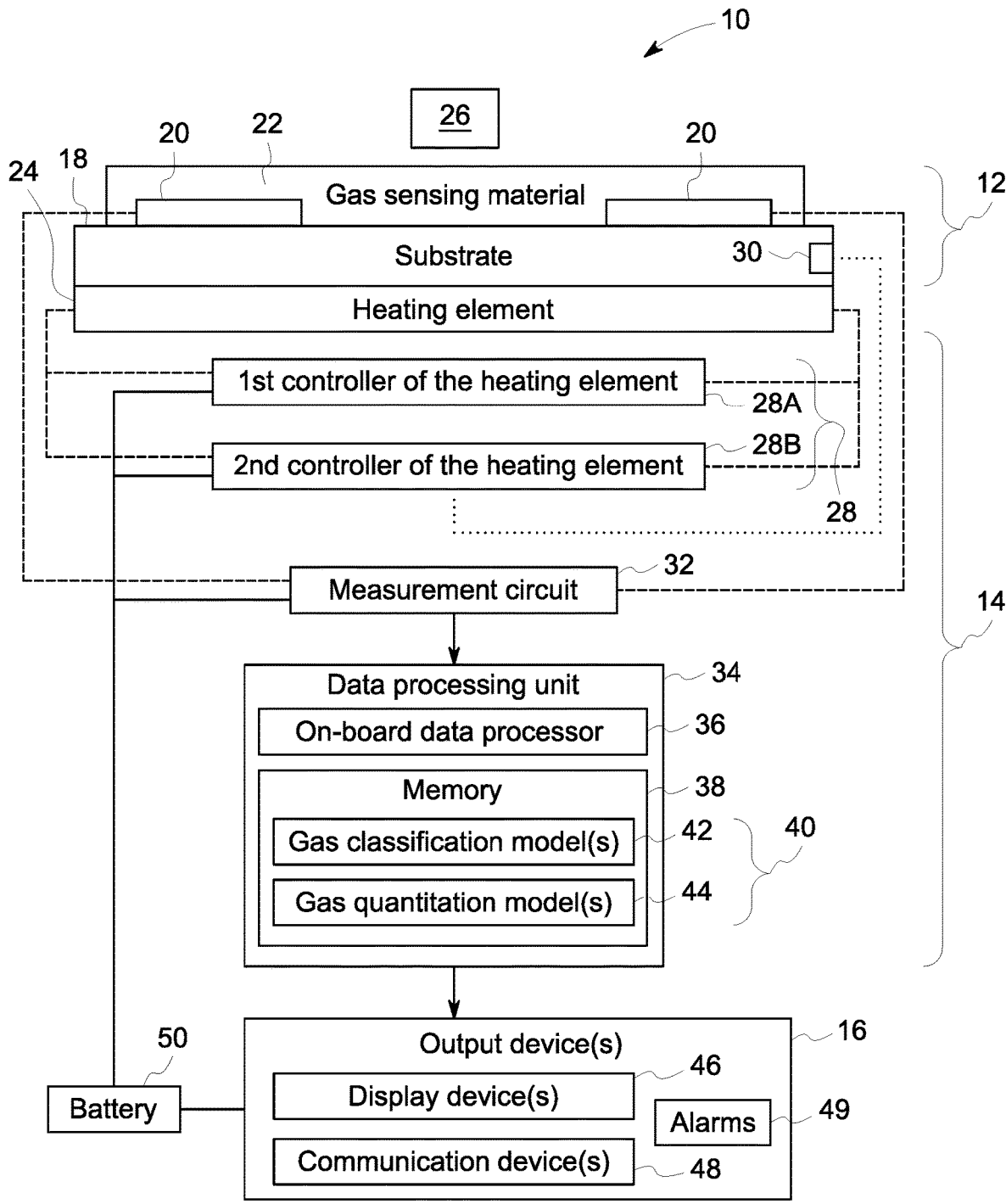
FIG. 1 is a schematic diagram of an embodiment of a gas sensor for multi-gas analysis of fluid samples, in accordance with aspects of the present technique.

Present embodiments are directed to a system and a method for multi-gas sensing using dielectric excitation of a single metal oxide semiconductor sensing material arranged as a single gas sensing element. It may be noted that metal oxide semiconductor sensing materials are often abbreviated in the industry as metal oxide semiconductor (MOS) materials or semiconducting metal oxide (SMOX) or semiconducting metal oxide (MOX) materials. Traditional MOS-based gas sensors measure only a direct current (DC) resistance response. A measurement of a single response per sensor is also known as a single-output readout. While traditional MOS-based gas sensors measure direct current (DC) resistance responses at a number of different temperatures to differentiate multiple gases in a fluid sample, it is presently recognized in this disclosure that measuring dielectric excitation responses of a MOS-based gas sensor at a constant operating temperature can offer distinct advantages, such as enhanced selectivity and enhanced operational lifetime of the sensor. That is, it is presently recognized that, at a constant operating temperature, the impedance spectrum of a MOS-based sensing element is differently affected by different gases, and such desired differences are more pronounced as compared to the resistance response of the same sensing element, even when multiple operating temperatures are used. Thus, present embodiments unexpectedly demonstrate MOS-based gas sensors that can differentiate between different gases at a single operating temperature, wherein this differentiation is superior in the differentiation between different gases and in baseline stability, as compared to the resistance response of the same sensing element operated at more than one operating temperature.

As noted above, traditional MOS-based gas sensors typically measure DC resistance responses of a MOS-based sensing element at two or more operating temperatures when performing multi-gas analysis of a fluid sample. In contrast, present embodiments of gas sensors include a MOS-based sensing element that interacts with gases in a fluid sample at a constant operating temperature and provides impedance responses to particular dielectric excitation frequencies, wherein these dielectric excitation responses of the MOS-based sensing element are measured and analyzed to differentiate two or more gases in a fluid sample. As used herein, the terms "analyte", "analyte gas", or "analyte fluid" refer to a component of interest in the measured fluid. As used herein, the term "interferent", "interference gas", "interference fluid" refers to any component in the measured fluid that can undesirably affect the accuracy and precision of measurements of the analyte with the sensor. A gas sensing element that provides impedance responses to more than one dielectric excitation frequency, wherein these impedance responses of the gas sensing element are measured and analyzed to differentiate two or more analyte gases in a fluid sample can be called a multivariable gas sensing element. A multivariable gas sensing element has two or more responses or outputs. A multivariable gas sensing element has a multi-output readout.

With the foregoing in mind, FIG. 1 is a schematic diagram of an embodiment of a gas sensor 10 for multi-gas analysis of fluid samples, in accordance with the present technique. In different embodiments, the gas sensor 10 may be a wearable multi-gas sensor, an ingestible gas sensor, or a tattooed gas sensor for personal (e.g., patient) monitoring. In certain embodiments, the gas sensor 10 may be an industrial environmental sensor, an asset monitoring sensor, an industrial process monitoring gas sensor, a consumer sensor, a transportation sensor, a security sensor, or any combination thereof.

For the embodiment illustrated in FIG. 1, the gas sensor 10 generally includes at least one gas sensing element 12, control circuitry 14, and one or more output devices 16. Each gas sensing element 12 of the gas sensor 10 includes a substrate 18 having sensing electrodes 20 disposed thereon, as well as a gas sensing material 22 (e.g., a suitably formulated metal oxide semiconductor material (MOS) applied to form a gas sensing film) disposed on the substrate 18 between the sensing electrodes 20. In certain embodiments, the gas sensor 10 may include multiple gas sensing elements 12 (e.g., an array of gas sensing elements 12), such as gas sensing elements having different MOS-based gas sensing materials 22. In some embodiments, a single gas sensing element 12 may include multiple gas sensing materials 22 (e.g., an array of gas sensing materials 22), each having a respective set of sensing electrodes 20 for performing electrical measurements. In certain embodiments, there may be more than two sensing electrodes 20, and the sensing electrodes 20 may include a plurality of interdigitated sensing electrodes. It may be appreciated that the gas sensing material 22 is generally applied onto the electrodes 20 to form the gas sensing film, such that the dielectric excitation of the gas sensing material 22, as well as the measurement of the excitation responses of the gas sensing material 22, is performed via the electrodes 20.

Additionally, a resistive heating element 24 is disposed on a surface of the substrate 18, opposite the gas sensing material 22, and is designed to heat the gas sensing material 22 to a suitable operating temperature during multi-gas analysis of a fluid sample 26. In certain embodiments, the heating element 24 may be disposed on a surface of the substrate 18 that is opposite the gas sensing material 22, while in other embodiments, the heating element 24 may be disposed on the same surface of the substrate 18 as the gas sensing material 22. For embodiments with multiple gas sensing elements 12, in certain cases, more than one gas sensing material 22 may be applied to a common substrate to form the multiple gas sensing elements 12 on a common substrate 18, which may be heated by a single heating element, while in other cases, each gas sensing material 22 may be disposed on a respective substrate 18 with a respective heating element 24. Additionally, in certain embodiments, the heating element 24 may be integrated into the substrate 18 as a monolithic structure.

During operation of the gas sensor 10, the gas sensing material 22 of the gas sensing element 12 is heated to a constant operating temperature as the gas sensing material 22 is exposed to the fluid sample 26, which may include one or more analyte gases or at least one analyte gas and at least one interference gas. As such, the control circuitry 14 of the illustrated gas sensor 10 includes one or more heating element controllers 28 electrically connected to the heating element 24, and that controls the heating element 24 and achieves the constant operating temperature. In different embodiments, this electrical connection can be independent, or galvanically connected in parallel or in series. For embodiments with multiple gas sensing elements 12 having distinct heating elements 24, each of the heating elements 24 may be controlled by the one or more heating element controllers 28 to achieve the constant operating temperature.

For the illustrated embodiment, the first controller 28A of the heating element 24 is calibrated during manufacturing to provide a predetermined constant or static voltage to the heating element that, under the calibration conditions, is sufficient to achieve a desired operating temperature. However, it is presently recognized that this predetermined constant voltage provided by the first controller 28A may not heat the gas sensing material 22 to the desired operating temperature in all circumstances. For example, the heating element 24 may age over the operational lifetime of the gas sensor 10, and this may result in the heating element 24 producing less heat in response to the predetermined constant voltage provided by the first controller 28A. Additionally, certain measurement environments may be substantially colder than the measurement environment in which the gas sensor 10 was calibrated, and this may result in the gas sensing material 22 being unable to reach the desired operating temperature in response to the predetermined constant voltage provided by the first controller 28A.

With this in mind, for the illustrated embodiment, the second controller 28B of the heating element 24 is a feedback controller that is designed to provide an additional adjustable or variable voltage to the heating element 24, such that the combination of the predetermined constant voltage and the additional adjustable voltage heats the gas sensing material 22 to the desired constant operating temperature, regardless of the age of the heating element or the ambient conditions (e.g., temperature, humidity) of the fluid sample 26 being analyzed. As used herein, an "operating temperature" is the temperature of each gas sensing element 12 (e.g., the gas sensing material 22, substrate 18) of the gas sensor while electrical measurements are performed. For example, in certain embodiments, the second controller 28B determines feedback by measuring a current flow through the heating element 24 as a result of the predetermined constant voltage provided by the first controller 28A, and in response to determining that the current is below a predetermined threshold value, provides additional voltage to the heating element 24 until the desired current is reached. In some embodiments, the second controller 28B may be communicatively coupled to a temperature sensor 30 in an operational contact with the gas sensing element 12 to receive feedback regarding an actual temperature of the gas sensing material 22, and in response to determining that the temperature of the gas sensing material 22 is below a predetermined operating temperature, provide additional voltage to the heating element 24 until the desired operating temperature is reached. In some embodiments, the second controller 28B may be communicatively coupled to an electrical current sensor or an electrical resistance sensor of the gas sensing element 12 to monitor performance of the heating element 24. As such, by working in concert to control the heating element 24, the controllers 28 of the heating element 24 ensure that the gas sensing material 22 is maintained at the desired constant operating temperature, regardless of the operational age of the gas sensor 10 or the ambient conditions of the fluid sample 26. For example, in certain embodiments, the constant operating temperature of the gas sensing material 22 may be between 30° C. and 1000° C., between 50° C. and 900° C., or between 80° C. and 600° C. Additionally, in certain embodiments, the operating temperature may vary by less than 50%, more preferably varies by less than 30%, and most preferably varies by less than 20%, while the gas sensing material 22 contacts the fluid sample 26. The operating temperature may undesirably vary over time due to different aspects, such as aging of the heating element and variation of ambient conditions around the heating element. The disclosed designs are intended to address this variation that may otherwise be present.

For the illustrated embodiment, the sensing electrodes 20 of the gas sensing element 12 are electrically coupled to a measurement circuit 32 of the control circuitry 14 of the gas sensor 10. The measurement circuit 32 is designed to provide at least dielectric excitation to the gas sensing material 22 at preselected frequencies and to measure excitation responses of the gas sensing material 22 (e.g., impedance responses, DC responses) at these excitation frequencies. In certain embodiments, the measurement circuit 32 may additionally be capable of (or designed to) provide a direct current (DC) excitation to the gas sensing material 22 and to measure the DC response (e.g., resistance response) of the gas sensing material 22 to this DC excitation. In certain embodiments, the measurement circuit 32 may measure both alternating current (AC) and DC responses of the gas sensing material 22. However, in certain embodiments, the measurement circuit 32 may be designed to only provide dielectric excitation to, and only measure dielectric responses of, the gas sensing material 22.

As used herein, "dielectric excitation" of a MOS sensing material refers to an alternating current (AC) excitation of the MOS sensing material at a shoulder of its dielectric relaxation region. As used herein, "impedance" is a non-limiting term for any electrical response of the sensing system to an alternating electrical current applied to the gas sensing material 22. It may be appreciated that such a response may be measured as different electrical properties in different embodiments. Non-limiting examples of these electrical responses of the gas sensing material 22 to alternating electrical current include: impedance, real part of impedance, imaginary part of impedance, admittance, reactance, susceptance, or the like. In the present specification, examples of the responses are given as impedances; however, other electrical responses of the gas sensing material 22 to alternating electrical current excitation may be also equally produced. In one embodiment, the electrical response of the gas sensing material 22 may be monitored at the gas-modulated high-frequency shoulder of the dielectric relaxation peak of the sensing material. In one embodiment, the electrical response of the sensing system may be monitored at the gas-modulated low-frequency shoulder of the dielectric relaxation peak of the sensing material.

The gas sensor 10 may represent one or more different versions of multi-gas sensing systems described herein. In one or more embodiments, the measurement circuit 32 may include a resistor-capacitor (RC) electrical circuit that includes one or more resistor (R) and capacitor (C) components that may be electronically changed by a controller circuitry 14 by the presence of one or more analyte gases of interest. In one or more embodiments, the measurement circuit 32 may perform dielectric excitation and impedance measurements at one or more different frequencies or at one or more different RC configurations of the measurement circuit 32. For example, the measurement circuit 32 of the gas sensor 10 may measure impedance responses of the gas sensing material 22 at different frequencies, at different resistances of the RC electrical circuit of the measurement circuit 32, at different capacitances of the RC electrical circuit of the measurement circuit 32, or any combination of two or more therein. The measurement circuit 32 provides excitation and measurements of the response of the gas sensing element 12 to gases. The measurement circuit 32 is not designed to be affected by the measured gas concentrations. Rather, only the gas sensing element 12 is designed to be predictably affected by the measured gas concentrations.

The control circuitry 14 of the illustrated gas sensor 10 includes a data processing unit 34 (also referred to herein as data processing circuitry) that is communicatively coupled to the measurement circuit 32 to receive the excitation responses measured by the measurement circuit 32. The data processing unit 34 includes an on-board data processor 36 and a memory 38 storing gas analysis models 40, including analyte gas classification models 42, analyte gas quantitation models 44, or any combination thereof. These gas analysis models 40 are mathematical models that generally store relationships between excitation responses (e.g., impedance responses, DC responses) and particular classifications or concentrations of analyte gases in a fluid sample. For example, the gas classification models 42 may store relationships between excitation responses of the gas sensing material 22 and particular classifications of analyte gases, while the gas quantitation models 44 may store relationships between excitation responses of the gas sensing material 22 and particular concentrations of analyte gases. In certain embodiments, the gas analysis models 40 may include one or more coefficients having values that are experimentally determined and stored in the memory 38. In some embodiments, the number of analyte gases determined by the analyte gas classification models 42, or analyte gas quantitation models 44, or any combination thereof, for the illustrated gas sensor 10 may range from one analyte gas to ten analyte gases, to fifty analyte gases, and to hundreds of analyte gases. A gas sensing element 12 that has two or more responses or outputs is called a multivariable gas sensing element. To analyze outputs from a multivariable gas sensing element, multivariate data processing principles are applied. Multivariate data processing principles can be applied to quantify diversity of responses of a multivariable sensor to different gases. Multivariate transfer functions can be built to quantify different gases. The built multivariate transfer functions can be implemented to quantify different gases in new measurement data from this multivariable gas sensing element.

Non-limiting examples of multivariate data processing principles include methods to perform classification/cluster analysis and quantitation of gases. Classification/cluster analysis can be performed to correctly determine the type of the analyte gas. Quantitation can be performed to correctly determine the concentration of the analyte gas. Examples of classification/cluster analysis algorithms include, but are not limited, to Principal Component Analysis (PCA), Hierarchical Cluster Analysis (HCA), Independent Component Analysis (ICA), Linear Discriminant Analysis (LDA), and Support Vector Machines (SVM) algorithm. Non-limiting examples of methods for performing analyte quantitation to determine the concentration of a particular analyte gas include Principal Component Regression (PCR), Independent Component Regression (ICR), Nonlinear Regression Analysis (NRA), Discriminate Function Analysis (DFA), or Artificial Neural Network Analysis (ANN). In certain aspects of the inventive subject matter described herein, a classification algorithm can be followed by quantitation algorithm.

As discussed below, the on-board data processor 36 receives the excitation responses measured by the measurement circuit 32, selects particular excitation responses (e.g., impedance responses, DC responses) for analysis, and provides these excitation responses as inputs to one or more of the stored gas analysis models 40, wherein the gas analysis models 40 return outputs that differentiate two or more analyte gases in the fluid sample 26. As used herein, "resolving" two or more gases in a fluid sample, or "providing resolution" between two or more gases in a fluid sample, or "differentiating" between two or more gases in a fluid sample refers determining a respective classification for each of the gases in the fluid sample, determining a respective concentration of the gases in the fluid sample, or determining both respective classifications and respective concentrations of gases in the fluid sample. As used herein, "classifying" or "determining a classification of" an gas refers to determining an exact chemical identity (e.g., acetylene, chlorine, ethylene oxide, nitrogen dioxide, sulfur dioxide, hydrogen, hydrogen chloride) of the gas or determining a chemical class (e.g., a hydrocarbon, alcohol, phenol, ether, aldehyde, ketone, carboxylic acid, ester, and so forth) to which each gas belongs. As used herein, "on-board" is used to describe the data processor 36 as being part of the control circuitry 14 integrated into the gas sensor 10, and is also used to describe "on-board" data processing, in which the on-board data processor 36 locally processes data, without sending the data to an external computing device for processing.

In certain embodiments, the memory 38 may be integrated into the on-board data processor 36. In certain embodiments, the on-board data processor 36 is a multicore processor. For example, in some embodiments, the on-board data processor 36 is a multicore processor on a single integrated circuit with two or more separate processing units (also referred to as cores), each of which reads and executes program instructions. In certain embodiments, the multicore processor may only include a single central processing unit (CPU) and multiple additional cores. For embodiments in which the on-board data processor 36 is a multicore processor, different gas analysis models and/or different signal processing algorithms may be independently executed by different cores to reduce the power consumption of the data processing unit 34 and/or the gas sensor 10.

For the illustrated embodiment, the gas sensor 10 includes one or more output devices 16. In certain embodiments, the output devices 16 include one or more display devices 46 that are configured to present information regarding a multi-gas analysis, such as the classification and/or concentration of two or more gases in the fluid sample 26. In some embodiments, other output devices 16 may include alarms 49, such as visual alarms (e.g., light emitting diodes (LEDs)), auditory alarms (e.g., speakers), and/or haptic alarms (e.g., haptic feedback devices). In certain embodiments, the output devices 16 may include one or more communication devices 48 (e.g., wired communication interfaces, wireless communication interfaces) that enable the gas sensor 10 to communicate with other computing systems, such as a desktop computer, a mobile computing device (e.g., a laptop, smart phone), a remote server (e.g., an Internet server, a cloud server), or other sensors (e.g., gas sensors, temperature sensors, vibration sensors, health monitors) of a multi-sensor monitoring system. For example, in certain embodiments, information determined by the on-board data processor 36 regarding the differentiation of two or more gases in the fluid sample 26 may be provided to an external computing system that serves as a controller of a mesh of sensors that includes the gas sensor 10. In some embodiments, the gas sensor may additionally or alternatively use the communication devices 48 to provide excitation response measurements to an external computing system, such that the external computing system can use these measurements to calculate one or more coefficient values for one or more of the gas analysis models and return these coefficient values to the gas sensor 10 for storage in the memory 38.

Additionally, the illustrated gas sensor 10 includes a battery 50 that is electrically coupled to provide power to various components of the gas sensor 10, including the control circuitry 14 and the output devices 16. It may be appreciated that the battery 50 should have a suitable capacity to power all of the components of the gas sensor 10. For example, this may include: heating the gas sensing material 22, providing dielectric excitation to the gas sensing material 22, measuring the dielectric excitation responses of the gas sensing material 22, analyzing the measured dielectric excitation responses to differentiate two or more gases in a fluid sample, and presenting results of the analysis via a suitable output devices 16. In certain embodiments, the battery 50 may have a capacity that is sufficient to operate the gas sensor 10 for at least 10 hours. In some embodiments, the battery 50 may have a battery capacity between 1 milliamp-hour (mAh) and 500 mAh, or between 1 mAh and 200 mAh, or between 1 mAh and 100 mAh. In certain embodiments, such as embodiments in which the gas sensor 10 is designed to be particularly thin (e.g., for ingestible or tattooed embodiments of the gas sensor 10), the battery 50 may have a thickness less than about 5 millimeters (mm). In some embodiments, all of the components of the gas sensor 10 may be coupled to or at least partially disposed within a suitable packaging or housing for a particular gas sensing application. For example, for personal monitoring applications, the packaging of the gas sensor 10 may be made of a biocompatible polymer that can be externally worn, subcutaneously injected, or ingested to perform personal or patient multi-gas analysis.

The gas sensor 10 may be a wearable device that may be worn or move from one place to another by an operator. The gas sensor 10 may be positioned in or be an integrated part of a helmet, hat, glove, or other clothing attributes. For example, the gas sensor 10 may be held within a wearable or non-wearable transferable object, such as a frame of military or industrial eyeglasses, a wearable pulse oximeter, a safety vest or harness, an article of clothing, a mobile device (e.g., a cellular phone, a tablet, or the like), or the like. The wearable device may be integrated into a fabric of the clothing, can be positioned on clothing such as on a pocket, can be in a form of an arm band, worn on a wrist or other extremity, or the like. The wearable device may be worn by a subject, such as a human or animal or a robot, may be removably coupled or integrated with an article worn by a subject (e.g., a shirt, pants, safety vest, safety personal protection clothing, eyeglasses, hat, helmet, hearing device, or the like), or may be any alternative device that may be transferrable such that sensor can be moved between different positions, may be stationary or substantially stationary, or the like. The wearable device may be worn, or otherwise carried, by different subjects or individuals, such as, but not limited to, soldiers, medical professionals, athletes, system operators, students, otherwise active or inactive individuals, or the like. Optionally, the wearable sensing system may be coupled with, integrated with, disposed on, or the like, an asset, such as a moving system such as a drone, a stationary system, or the like. The wearable systems may be positioned on items worn by the subject, such as helmets, pockets (e.g., of shirts, pants, bags, or the like), gloves, arm bands, ear pieces, or the like, or may be attached or otherwise coupled directly to the subject or asset, such as on the wrist, around an ankle, or the like. The wearable device can be fabricated using manufacturing technologies based on complementary metal-oxide-semiconductor electronics, flexible electronics, flexible hybrid electronics and other known approaches to provide conformal and flexible designs, implementations, and use. Optionally, the gas sensor 10 may be a stationary device, may be independently mobile (e.g., detachable from an operator and capable of moving independent of the operator), may be airborne, or the like.

The gas sensor 10 may be in contact with the fluid 26 in the form of a fluid vessel that may be a form of a vessel with controlled volume, or in the form of an open area such as an indoor facility (e.g., a room, a hall, a house, a school, a hospital, a confined space, or the like), or in the form of an outdoor facility (e.g., a stadium, a gas-production site, fueling stations, gasoline fueling stations, hydrogen fueling stations, compressed natural gas fueling stations, liquefied natural gas fueling stations, gas distribution site, fuel distribution site, a seashore, a forest, a city, urban environment, marine environment, or the like). In one embodiment, the gas sensor 10 may provide continuous monitoring of the fluid 26 within the reservoir or flow path. In one or more embodiments, the gas sensor 10 may be an impedance gas sensor, an electromagnetic sensor, an electronic sensor, a hybrid sensor, or another type of sensor. Optionally, the gas sensor 10 may be part of a sensor array.

The fluid 26 may be a gas, a liquid, a gas-liquid mixture, a solid, particles or particulate matter, or the like, containing one or more analyte gases therein. In another embodiment, the fluid 26 may be a gas or fuel, such as a hydrocarbon-based fuel. One example of the fluid 26 is natural gas or hydrogen gas that is supplied to a powered system (e.g., a vehicle, airplane engine, or a stationary generator set) for consumption. Other examples of such a fluid 26 can include gasoline, diesel fuel, jet fuel or kerosene, bio-fuels, petrodiesel-biodiesel fuel blends, natural gas (liquid or compressed), and fuel oils. Another example of the fluid 26 is indoor or outdoor ambient air. Another example of the fluid 26 is air at an industrial, residential, military, construction, urban, and any other known site. Another example of the fluid 26 is ambient air with relatively small concentrations of benzene, naphthalene, carbon monoxide, ozone, formaldehyde, nitrogen dioxide, sulfur dioxide, ammonia, hydrofluoric acid, hydrochloric acid, phosphine, ethylene oxide, carbon dioxide, hydrogen sulfide, chemical warfare agents such as nerve, blister, blood, and choking agents, hydrocarbons and/or other pollutants. Another example of the fluid 26 is a disinfection agent, such as alcohol, aldehyde, chlorine dioxide, hydrogen peroxide. Another example of the fluid 26 is ambient air with relatively small concentrations, medium concentrations, and large concentrations of flammable or combustible gases such as methane, ethane, propane, butane, hydrogen, and/or other gases. Another example of the fluid 26 is at least one gas dissolved in an industrial liquid such as transformer oil, bioprocess media, fermentation media, wastewater, and any other. Another example of the fluid 26 is the at least one gas dissolved in a consumer liquid such as milk, non-alcoholic beverages, alcoholic beverages, cosmetics, and any other. Another example of the fluid 26 is at least one gas (e.g., a biomarker) dissolved in a body liquid such as blood, sweat, tears, saliva, urine, and any other.

In certain embodiments, the fluid 26 may include analyte gases that are toxic industrial materials or toxic industrial chemicals. A non-limiting list of example toxic industrial materials and chemicals includes, but is not limited to, ammonia, arsine, boron trichloride, boron trifluoride, carbon disulfide, chlorine, diborane, ethylene oxide, fluorine, formaldehyde, hydrogen bromide, hydrogen chloride, hydrogen cyanide, hydrogen fluoride, hydrogen sulfide, nitric acid (fuming), phosgene, phosphorus trichloride, sulfur dioxide, sulfuric acid, and tungsten hexafluoride. In certain embodiments, the fluid 26 may include analyte gases that are toxic materials of the medium Hazard Index. A non-limiting list of example toxic materials of the medium Hazard Index includes, but is not limited to: acetone cyanohydrin, acrolein, acrylonitrile, allyl alcohol, allylamine, allyl chlorocarbonate, boron tribromide, carbon monoxide, carbonyl sulfide, chloroacetone, chloroacetonitrile, chlorosulfonic acid, diketene, 1,2-dimethylhydrazine, ethylene dibromide, hydrogen selenide, methanesulfonyl chloride, methyl bromide, methyl chloroformate, methyl chlorosilane, methyl hydrazine, methyl isocyanate, methyl mercaptan, nitrogen dioxide, phosphine, phosphorus oxychloride, phosphorus pentafluoride, selenium hexafluoride, silicon tetrafluoride, stibine, sulfur trioxide, sulfuryl chloride, sulfuryl fluoride, tellurium hexafluoride, n-octyl mercaptan, titanium tetrachloride, trichloroacetyl chloride, and trifluoroacetyl chloride.

In certain embodiments, the fluid 26 may include analyte gases that are toxic materials of the low Hazard Index. A non-limiting list of example toxic materials of the low Hazard Index includes, but is not limited to: allyl isothiocyanate, arsenic trichloride, bromine, bromine chloride, bromine pentafluoride, bromine trifluoride, carbonyl fluoride, chlorine pentafluoride, chlorine trifluoride, chloroacetaldehyde, chloroacetyl chloride, crotonaldehyde, cyanogen chloride, dimethyl sulfate, diphenylmethane-4,40-diisocyanate, ethyl chloroformate, ethyl chlorothioformate, ethyl phosphonothioic dichloride, ethyl phosphonic dichloride, ethyleneimine, hexachlorocyclopentadiene, hydrogen iodide, iron pentacarbonyl, isobutyl chloroformate, isopropyl chloroformate, isopropyl isocyanate, n-butyl chloroformate, n-butyl isocyanate, nitric oxide, n-propyl chloroformate, parathion, perchloromethyl mercaptan, sec-butyl chloroformate, tert-butyl isocyanate, tetraethyl lead, tetraethyl pyrophosphate, tetramethyl lead, toluene 2,4-diisocyanate, and toluene 2,6-diisocyanate.

In certain embodiments, the fluid 26 may include analyte gases that are indoor pollutants. A non-limiting list of example indoor pollutants includes, but is not limited to: acetaldehyde, formaldehyde, 1,3-butadiene, benzene, chloroform, methylene chloride, 1,4-dichlorobenzene, perchloroethylene, trichloroethylene, naphthalene, and polycyclic aromatic compounds. In certain embodiments, the fluid 26 may include analyte gases that are outdoor pollutants. A non-limiting list of example outdoor pollutants includes, but is not limited to: ozone, nitrogen dioxide, sulfur dioxide, and carbon monoxide.

Embodiments of the gas sensor 10 have the ability to differentiate gases at different concentrations in the fluid 26. For example, the gas sensor 10 may differentiate analyte gases at regulated vapor-exposure limits established by different organizations. In certain embodiments, the gas sensor 10 can differentiate analyte gases below a Permissible Exposure Limit (PEL). In some embodiments, the gas sensor 10 can differentiate analyte gases below Threshold Limit Value Short-Term Exposure Limit (TLV-STEL). In some embodiments, the gas sensor 10 may differentiate analyte gases below Threshold Limit Value Time-Weighted Average (TLV-TWA). In some embodiments, the gas sensor 10 may differentiate analyte gases below Immediately Dangerous to Life or Health (IDLH). In certain embodiments, the gas sensor 10 may differentiate analyte gases below and above Lower Explosive Limit (LEL). In certain embodiments, the gas sensor 10 may be capable of differentiating analyte gases having a concentration less than 5%, less than 100 part-per-million (ppm), less than 100 part-per-billion (ppb), less than 100 part-per-trillion (ppt).

Figure 2:
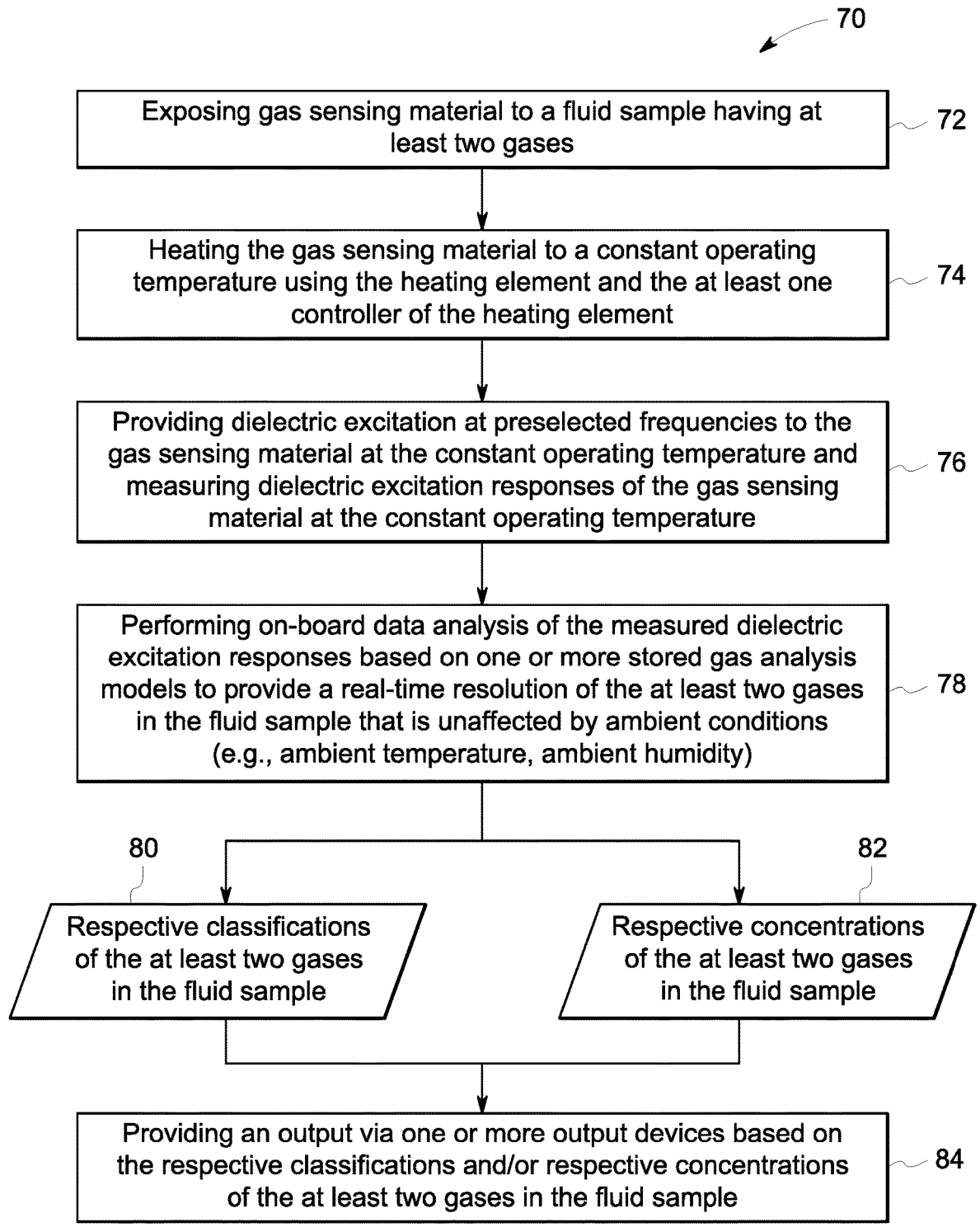
FIG. 2 is a flow diagram illustrating an embodiment of a process whereby the gas sensor performs multi-gas analysis, in accordance with aspects of the present technique.

FIG. 2 is a flow diagram illustrating an embodiment of a process 70 whereby the gas sensor 10 performs multi-gas analysis of a fluid sample 26. The process 70 begins with exposing (block 72) the gas sensing material 22 of the gas sensing element 12 to a fluid sample having at least two gases (e.g., at least two analyte gases, at least one analyte gas and one interference gas). For example, the entire gas sensor 10, or only the gas sensing element 12 of the gas sensor 10, may be exposed to the fluid sample. The process 70 includes heating (block 74) the gas sensing material 22 to a constant operating temperature using the one or more heating element controllers 28. As discussed above, in certain embodiments, the first controller 28A of the heating element 24 provides a predetermined constant voltage to the heating element 24, while the second controller 28B of the heating element 24 provides an additional adjustable voltage to the heating element 24, such that the combined heating element voltage results in the gas sensing material 22 maintaining the desired constant operating temperature. Typically, the gas sensing material 22 is heated before, during, and after that it is exposed to the fluid sample 26.

Once the gas sensing material 22 has been exposed to the fluid sample 26 and heated to the constant operating temperature, the process 70 proceeds with the measurement circuit 32 providing (block 76) dielectric excitation using at least two preselected frequencies to the gas sensing material 22 operating at the constant operating temperature, and then measuring dielectric excitation responses (e.g., impedance responses) of the gas sensing material 22. In certain embodiments, the measurement circuit 32 may additionally apply DC excitation to the gas sensing material 22 and measure the DC excitation response (e.g., resistance response) of the gas sensing material 22 at the constant temperature. However, in some embodiments, the measurement circuit 32 may only measure impedance responses of the gas sensing material 22 as it contacts the fluid sample 26 at the constant operating temperature.

Traditionally, MOS gas sensors 10 measure a DC resistance response of a MOS-based sensing element 12 and relate the measured DC resistance response to a concentration of a gas using a power-law relation between the measured resistance and gas concentration. Such DC resistance responses from a MOS gas sensor 10 may be provided as a signal output (e.g., to a user) in a form of an analog signal. Depending on the design of an analog circuit, an analog signal from a MOS gas sensor 10 may represent linear resistance, logarithmic resistance, or conductivity. Alternatively DC resistance responses from a traditional MOS-based gas sensor 10 may be provided as a signal output in a form of a digitized DC resistance response signal.

Dependent upon the design of an analog/digital circuit, the digital signal from a MOS gas sensor 10 may be correlated with linear resistance, logarithmic resistance, or conductivity. A digital signal from a MOS gas sensor 10 that is correlated with its DC resistance response can be provided (e.g., to the user) by any of digital communication protocols, for example an I2C (Inter-Integrated Circuit), alternatively known as IIC, and any other communication protocols.

For the illustrated embodiment, the process 70 continues with the on-board data processor 36 of the gas sensor 10 performing (block 78) on-board data analysis of the measured dielectric excitation responses based on at least one of the stored gas analysis models 40 to provide a real-time resolution (e.g., real-time differentiation) of the gases in the fluid sample. In some embodiment, a real-time resolution or differentiation of the gases in the fluid sample is unaffected by ambient conditions (e.g., ambient temperature, ambient humidity, ambient pressure). For certain embodiments in which DC excitation response is also measured by the measurement circuit 32, the on-board data processor 36 may also provide this DC excitation response as an input to at least one of the stored gas analysis models 40 when differentiating the gases in the fluid sample. In this context, "real-time" refers to the on-board data processor 36 of the gas sensor 10 being able to locally, rapidly differentiate gases in the fluid sample without requiring the measured excitation responses be provided to an external computing system for processing.

For the embodiment of the process 70 illustrated in FIG. 2, after differentiating the gases in the fluid sample 26, the gas sensor 10 may use one or more output devices 16 to provide an output (block 84) based on the respective classifications 80 of the gases in the fluid sample, the respective concentrations 82 of the gases in the fluid sample, or both. For example, one or more output devices 16 of the gas sensor 10 may present or display the respective classifications 80 and/or the respective concentrations 82 of the gases in the fluid sample 26. In certain embodiments, the gas sensor 10 may provide the respective classifications 80 and/or the respective concentrations 82 of the gases to an external computing system via one or more suitable communication devices 48 (e.g., a wireless communication interface) of the gas sensor 10. In certain embodiments, the gas sensor 10 may use one or more output devices 16 to output the respective alarms 49 of the presence of gases in the fluid sample above certain predetermined threshold levels stored in the memory 38 of the gas sensor 10.

Figure 3:
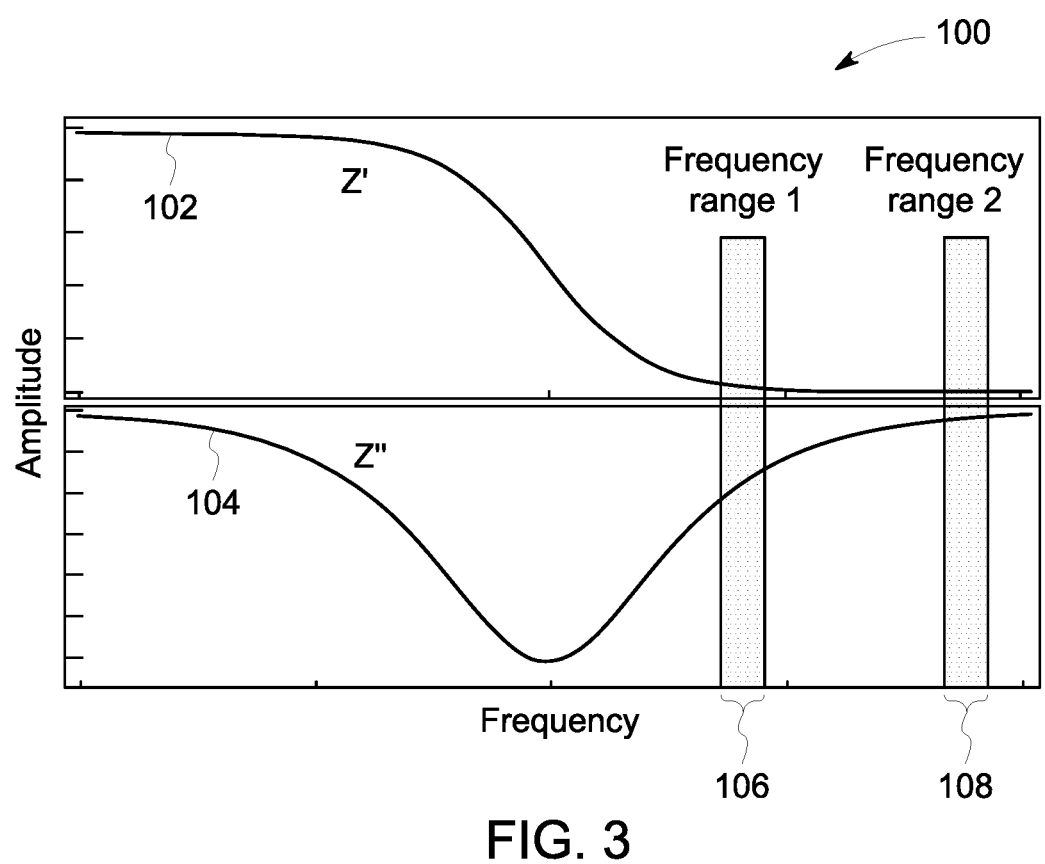
FIG. 3 is a graph of an example impedance spectrum of a gas sensing material of the gas sensor after applying dielectric excitation over the range of preselected frequencies, in accordance with aspects of the present technique.

FIG. 3 is a graph illustrating an example impedance spectrum 100. In impedance spectroscopy, measurements of the real part Z' and the imaginary part Z" of the impedance may be performed over a broad range of frequencies to determine the shape of the impedance spectrum 100 of the gas sensor 10. As illustrated, the impedance spectrum includes two curves, each representing part of the impedance response of the gas sensor 10 over a broad range of frequencies to determine the shape of the impedance spectrum. In particular, a first curve 102 represents the real part (Z') of the impedance of gas sensor 10, while a second curve 104 represents the imaginary part (Z") of the impedance of the gas sensor 10 as measured over a broad range of frequencies. Unlike broad-band impedance spectroscopy measurements, the dielectric excitation measurements are performed over specific frequency ranges by following the front (high- or low-frequency) shoulder of the dielectric relaxation region obtained from impedance measurements of (n- or p-type, respectively) MOS materials when they are exposed to various gas concentrations.

For present embodiments, the measurement circuit 32 is or includes an impedance detector that measures the dielectric excitation response of the gas sensor 10 at two or more frequency ranges 106, 108 (which may or may not be disposed in the "dielectric relaxation region" of the gas sensor 10). For example, in certain embodiments, each dielectric excitation response measured by the measurement circuit 32 may include a combination (e.g., a sum, a difference, any other mathematical representation) of a value from the first curve 102 (e.g., a real impedance value) and a value from the second curve 104 (e.g., an imaginary impedance value), both selected from the frequency ranges 106, 108. Alternatively, in some embodiments, each dielectric excitation response measured by the measurement circuit 32 may include a combination (e.g., a sum, a difference, any other mathematical representation) of a value from the first curve 102 (e.g., a real impedance value Z') and a value from the second curve 104 (e.g., an imaginary impedance value Z"), both selected from the frequency ranges 106, 108, or other frequency ranges. Selection of the frequency ranges 106, 108 may depend on type of the gas sensing element 12 of the gas sensor 10. For example, related to the gas sensing element 12, the selection of the frequency ranges 106, 108 may depend on the type of the MOS sensing material, for example n-type or p-type or a combination of n- and p-type MOS sensing material and type of gases for measurements such of reducing gases or oxidizing gases. As a result, either the high-frequency shoulder region or the low-frequency shoulder region may be selected for measurements.

It may be appreciated that, for present embodiments, the dielectric excitation measurements represented in FIG. 3 are performed at a constant operating temperature in order to achieve multi-gas differentiation. This is in contrast to traditional MOS-based gas sensors that collect resistance measurements (e.g., DC excitation response) in order to achieve multi-gas differentiation. That is, for traditional MOS-based gas sensors, in order to achieve multi-gas differentiation, the resistance responses of the MOS-based gas sensor contacting the fluid sample are measured at two or more different temperatures. It may be appreciated that there are numerous advantages to operating the disclosed gas sensor 10 at a constant operating temperature in order to achieve multi-gas differentiation. For example, temperature modulation involves a substantial effort for synchronization of heating cycles with the data analytics interpretations.

Additionally, it is presently recognized that the continual temperature cycling of traditional MOS-based gas sensors undesirably ages heating elements and limits the operational lifetime of these sensors. Furthermore, it is recognized that the temperature switching of traditional MOS-based gas sensors can negatively impact the quality of the electrical measurements by introducing undesirable instabilities, noise, and hysteresis. Moreover, though unexpected, it is presently recognized in this disclosure that, for the disclosed gas sensor 10 operating at the constant operating temperature, the dielectric excitation response at certain frequencies of the sensor dielectric relaxation spectrum provides a superior multi-gas differentiation and baseline stability, as compared to the resistance response of the same gas sensing material 22 over several different operating temperatures.

Experimental Example 1

To further demonstrate the superior performance of the disclosed technique, experiments were performed to compare the ability of conventional DC/resistance measurements versus dielectric excitation measurements for the differentiation between different analyte gases in fluid samples. For these experiments, all measurements were performed using a tin oxide ($SnO_2$) as the gas sensing material 22. The measurements were performed by the measurement circuit 32 as either DC excitation responses (e.g., resistance measurements), or as dielectric excitation responses (e.g., impedance measurements) selected from the high-frequency shoulder region 106 of corresponding dielectric relaxation spectra 100 after dielectric excitation. FIGS. 4-10 correspond to a first example of operation of the gas sensor 10 when measured with its resistance response and under dielectric excitation.

Certain measurements were performed with a total or combined heating element voltage from the one or more heating element controllers 28 of either 4.5 volts (V) or 5.0 volts (V), as indicated below. For the embodiment of the gas sensor 10 used for these experiments, the 4.5 V total heating element voltage corresponds to an operating temperature of about 250 degrees Celsius (° C.), while the 5.0 V total heating element voltage corresponds to an operating temperature of about 300° C. For the experiments, the gas sensing element 12 of the gas sensor 10 was exposed to each analyte gas at four different concentrations. Three analyte gases were utilized, including acetylene (first analyte gas, gas 1), hydrogen (second analyte gas, gas 2), and water vapor (third analyte gas, gas 3). The four different concentrations of the first analyte gas were: 2300 parts-per-million (ppm), 4600 ppm, 6900 ppm, and 9200 ppm; the four different concentrations of the second analyte gas were: 1.88 ppm, 3.75 ppm, 5.63 ppm, and 7.50 ppm; and the four different concentrations of the third analyte gas were: 10% relative humidity (RH), 20% RH, 30% RH, and 40% RH. Additionally, for the experiments represented by FIGS. 4-7, the gas sensing material 22 of the gas sensor 10 was: (A) heated to a first operating temperature, (B) exposed to each of the four concentrations of the first analyte gas, (C) exposed to each of the four concentrations of the second analyte gas, (D) exposed to each of the four concentrations of the third analyte gas. Thereafter, the gas sensor 10 was then heated to a second operating temperature, and steps B-D were repeated again at the second operating temperature.

Figure 4:
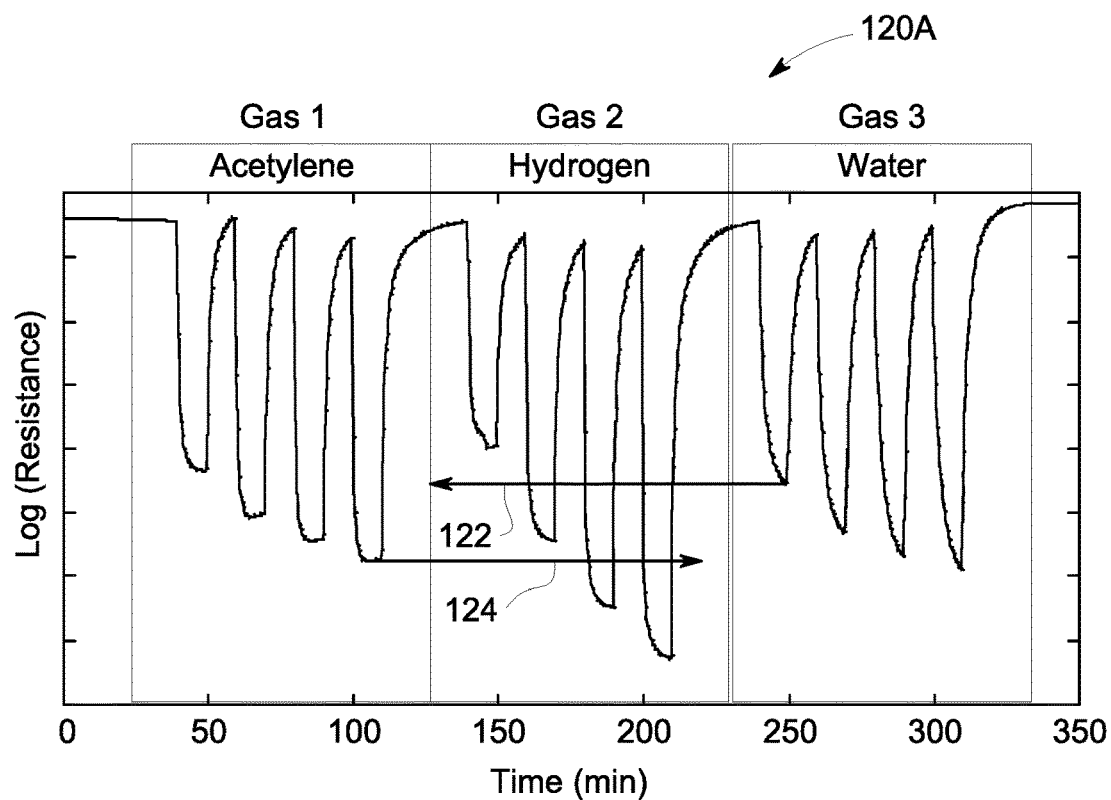
FIG. 4 is a graph depicting an example of a temperature-dependent chemiresistor response pattern of the gas sensing material to three analyte gases at a first operating temperature, in accordance with aspects of the present technique.
Figure 5:
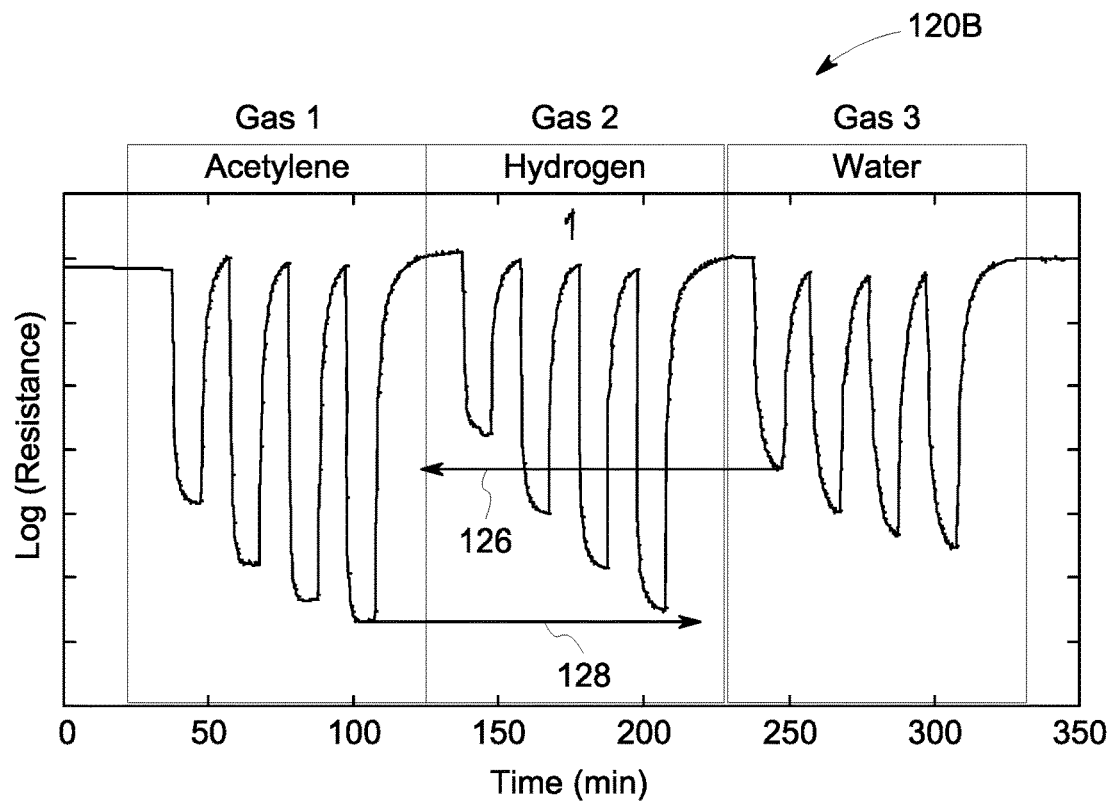
FIG. 5 is a graph depicting an example of a temperature-dependent chemiresistor response pattern of the gas sensing material to three analyte gases at a second operating temperature, in accordance with aspects of the present technique.

FIGS. 4 and 5 are a set of graphs 120A and 120B depicting examples of temperature-dependent chemiresistor response patterns of the gas sensing material 22 to the three analyte gases at two different operating temperatures. More specifically, the plot 120A of FIG. 4 illustrates the raw resistance measurements (e.g., DC excitation response) collected by the measurement circuit 32 for each of the three analyte gases at the first heating element voltage (4.5 V) in a logarithmic resistance response scale. The plot 120B of FIG. 5 illustrates the raw resistance measurements (e.g., DC excitation response) collected by the measurement circuit 32 for each of the three analyte gases at the second heating element voltage (5.0 V) in a logarithmic resistance response scale.

Based on the data illustrated in FIG. 4, the gas sensing material 22 of the gas sensor 10 desirably demonstrates responses to each of the analyte gases. However, it is presently recognized that the resistance response pattern between second and third analyte gases was similar at both operating temperatures, while the response pattern between the first and second and between the first and third analyte gases was different at the different operating temperatures. The horizontal arrows 122 and 124 in FIG. 4 and the horizontal arrows 126 and 128 in FIG. 5 depict response patterns in a logarithmic resistance response scale between different gases. As illustrated, the response intensity to the highest concentration of gas 2 was higher than the response to the highest concentration of gas 1 at a heating element voltage of 4.5 V and the same at a heating element voltage of 5.0 V. However, the pattern of the resistance response to gas 2 and gas 3 was similar at two heating element voltages of 4.5 V and 5.0 V.

Figure 6:
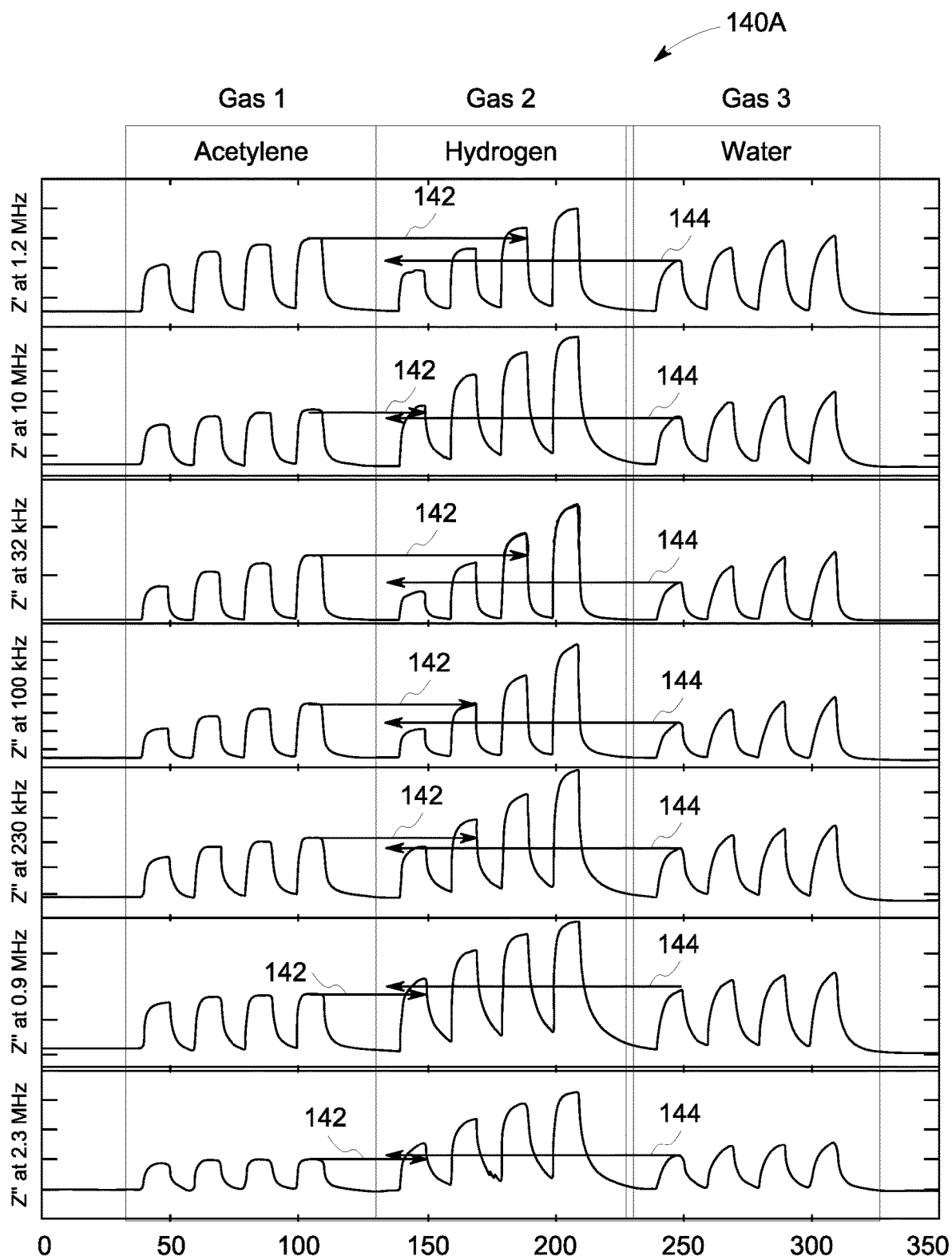
FIG. 6 is a set of graphs depicting temperature-dependent dielectric excitation response patterns of the gas sensing material to three analyte gases at seven operating frequencies as measured over the real part of impedance (Z') and over the imaginary part of impedance (Z") at a first operating temperature, in accordance with aspects of the present technique.
Figure 7:
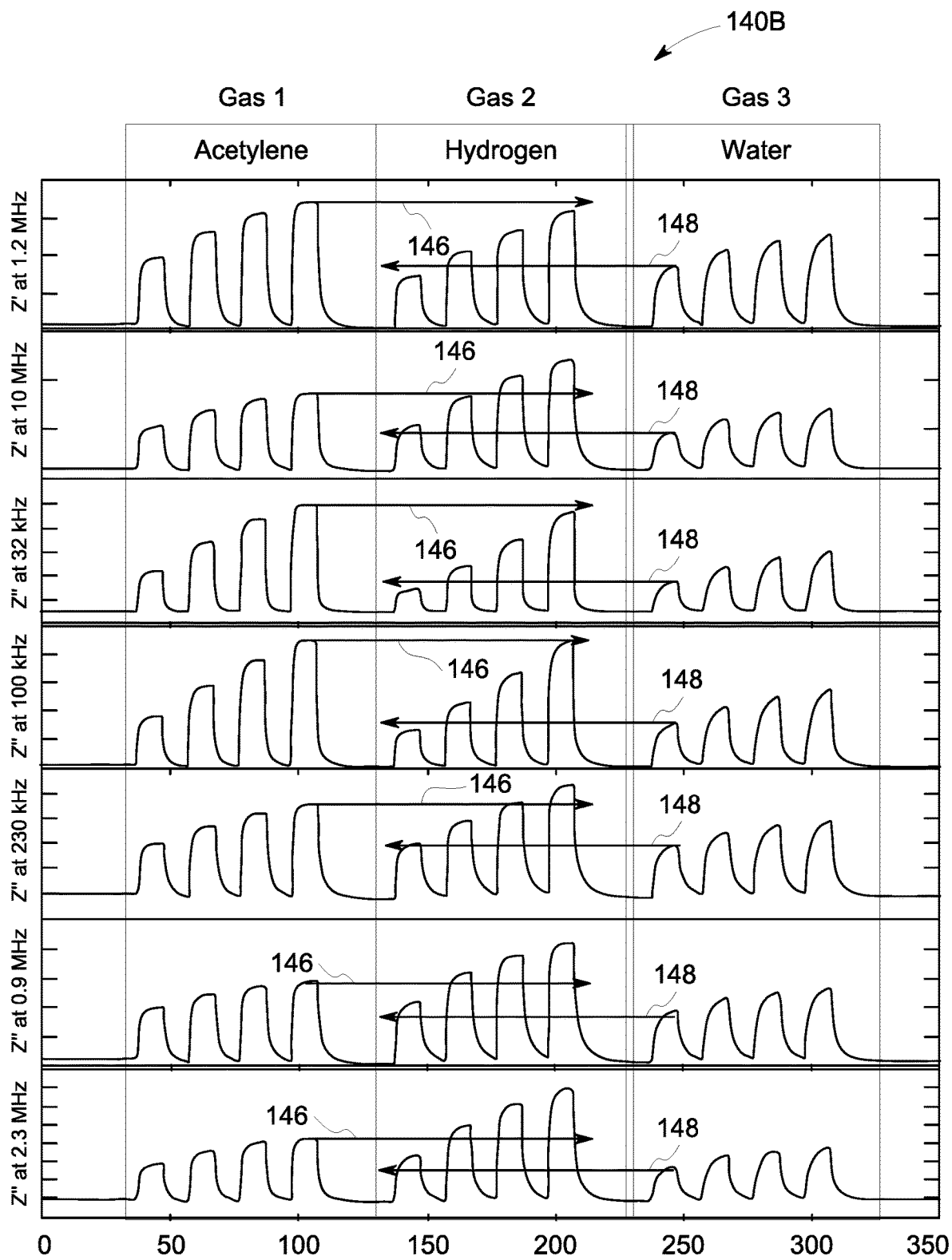
FIG. 7 is a set of graphs depicting temperature-dependent dielectric excitation response patterns of the gas sensing material to three analyte gases at seven operating frequencies as measured over the real part of impedance (Z') and over the imaginary part of impedance (Z") at a second operating temperature, in accordance with aspects of the present technique.

In contrast to FIGS. 4 and 5, FIG. 6 is a set of graphs 140A depicting dielectric excitation response patterns of the gas sensing material 22 to each of the three analyte gases at seven operating frequencies as measured over the real part of impedance (Z') and over the imaginary part of impedance (Z") at a first operating temperature. FIG. 7 is a set of graphs 140B depicting dielectric excitation response patterns of the gas sensing material 22 to each of the three analyte gases at seven operating frequencies as measured over the real part of impedance (Z') and over the imaginary part of impedance (Z") at a second operating temperature. The seven operating frequencies with the Z' and Z" measurements were Z' at 1.2 Megahertz (MHz), Z' at 10 MHz, Z" at 32 kHz, Z" at 100 kHz, Z" at 230 kHz, Z" at 0.9 MHZ, and Z" at 2.3 MHz.

The arrows 142 in FIG. 6 indicate that response to the highest concentration of gas 1 is either similar to the response of third concentration of gas 2 or it is less than the first concentration of gas 2. The arrows 144 in FIG. 6 indicate that response to the smallest concentration of gas 3 is either larger than the response of the first concentration of gas 2 or smaller than the response to the first concentration of gas 2. Thus, at a single operating temperature, the different frequencies of sensor operation at the real and imaginary parts of impedance provide a desired diversity in responses to all three gases.

The arrows 146 in FIG. 7 indicate that response to the highest concentration of gas 1 is either larger than the response of the fourth concentration of gas 2 or it is less than the second concentration of gas 2. The arrows 148 in FIG. 7 indicate that response to the smallest concentration of gas 3 is either larger than the response of the first concentration of gas 2 or smaller than the response to the first concentration of gas 2. Thus, at each individual operating temperature, the different frequencies of sensor operation at the real and imaginary parts of impedance provide a desired diversity in responses to all three analyte gases.

Figure 8:
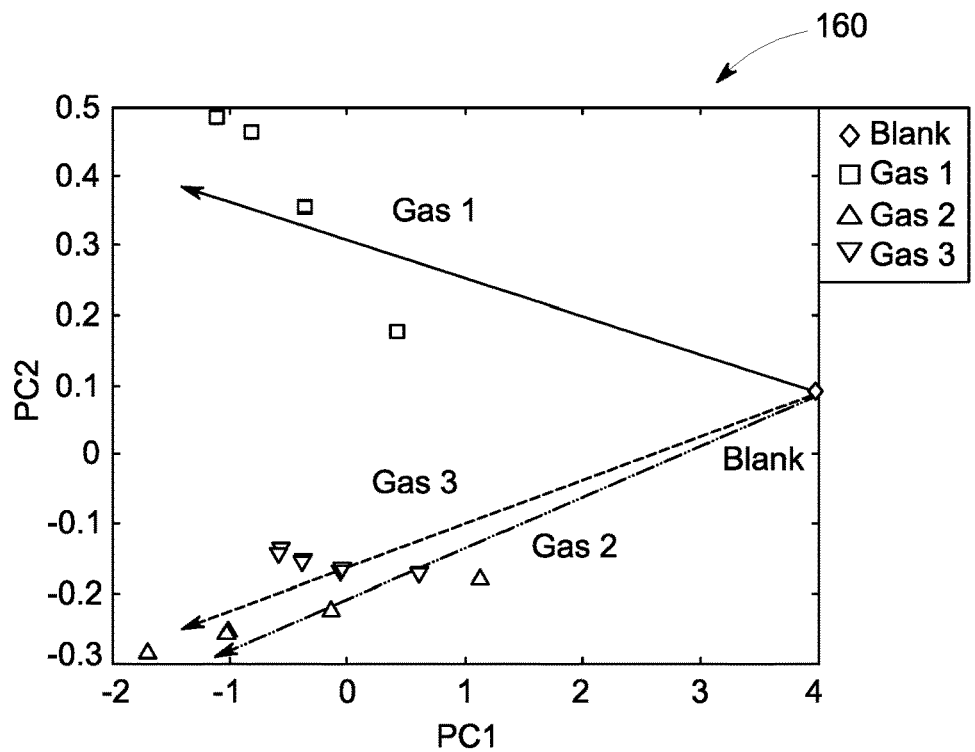
FIG. 8 depicts the results of principal component analysis (PCA) as a scores plot of the first two PCs of the resistance responses of FIGS. 4 and 5, in accordance with aspects of the present technique.

PCA was applied to analyze resistance responses (e.g., DC excitation responses) of FIGS. 4 and 5 to determine the ability of the gas sensor 10 to differentiate between the three analyte gases at the two operating temperatures. For each sensor state (different concentrations of three analyte gases and a blank), two data points were extracted from the raw dynamic response at the steady-state of the sensor response. FIG. 8 depicts the results of PCA as a scores plot 160 of the first two PCs of the logarithmic resistance responses from FIGS. 4 and 5. For analysis of resistance responses, typically logarithmic scale is utilized because of the highly non-linear resistance response that follows the power law between the MOS resistance and the concentration of an analyte gas.

As illustrated by FIG. 8, the analysis of the logarithmic resistance responses from the plots 120 of FIGS. 4 and 5 by PCA demonstrates that responses to the three analyte gases were correlated with concentrations of the gases. However, in the scores plot 160 of FIG. 8, gas 2 and gas 3 were not adequately differentiated or resolved from one another. As such, the analysis of the logarithmic resistance responses did not provide a desired multi-gas differentiation, even when measured at more than one temperature.

Figure 9:
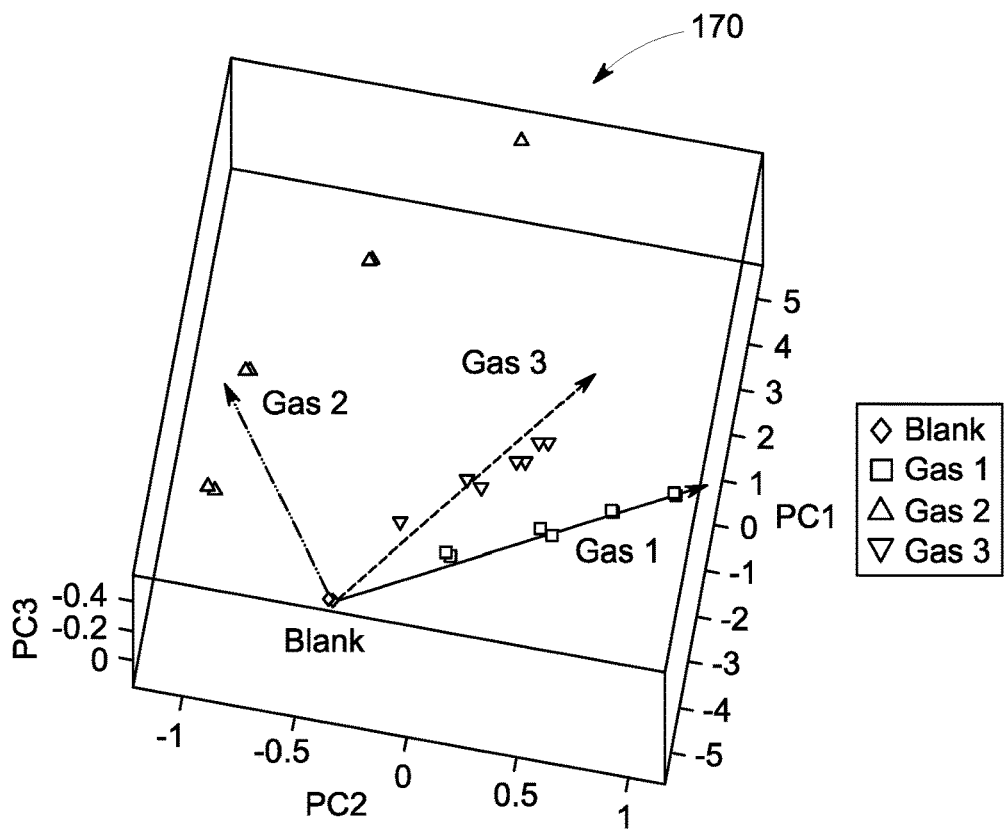
FIG. 9 depicts PCA results as a scores plots of the first three PCs (PC1 vs. PC2 vs. PC3) of the dielectric excitation responses of FIG. 6, in accordance with aspects of the present technique.

For comparison to the resistance measurements and analysis, PCA was also applied to analyze the dielectric excitation responses (e.g., impedance responses) of FIG. 6 to determine the ability of the gas sensor 10 to differentiate between the three analyte gases at a single operating temperature. FIG. 9 depicts PCA results as a scores plot 170 of the first three PCs (PC1, PC2, and PC3) of the dielectric excitation responses of the gas sensing material 22 at seven frequencies when operated at the single operating temperature. The single operation temperature in FIG. 9 corresponds to a heating element voltage of 4.5 V. More specifically, the scores plot 170 of FIG. 9 demonstrates clear differentiation between the three analyte gases. As such, FIG. 9 unexpectedly demonstrates differentiation between three gases under the dielectric excitations responses of the gas sensing material 22 and the respective concentrations of the three analyte gases, despite only a single operating temperature being used.

Figure 10:
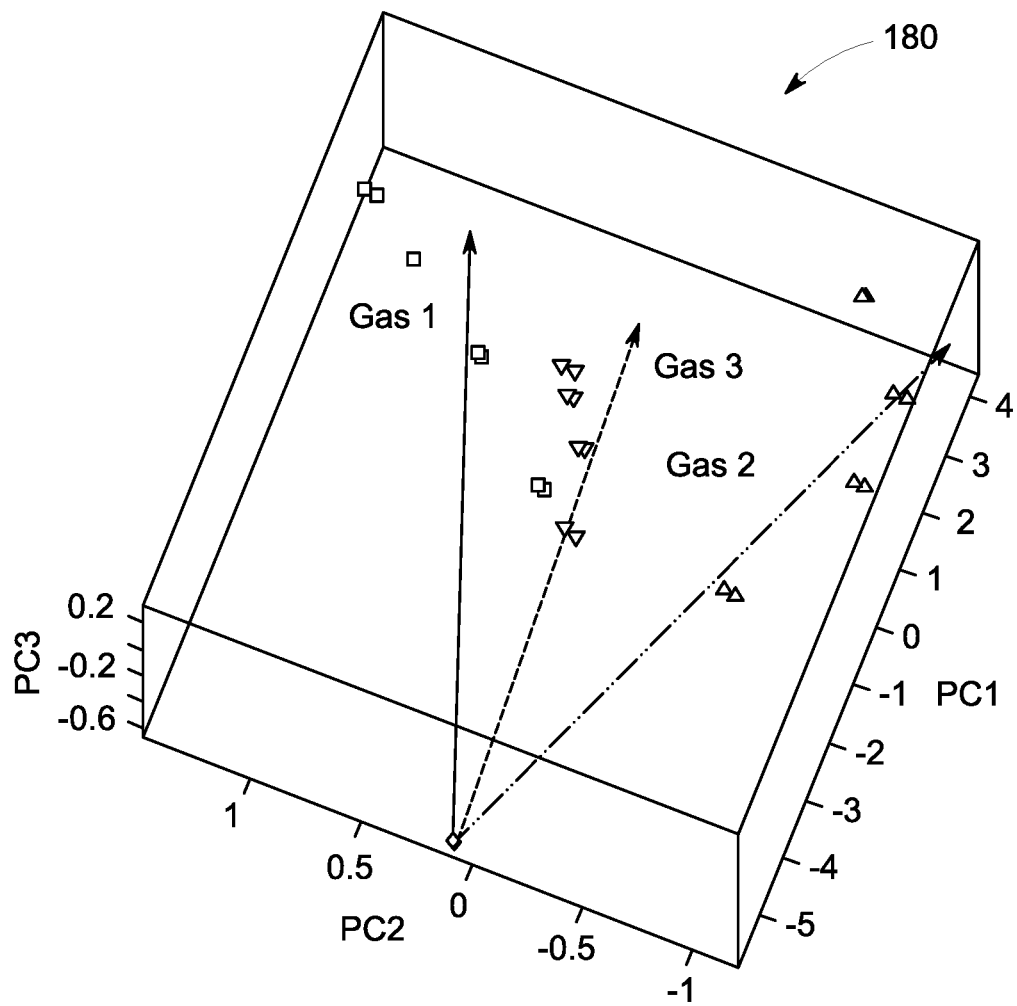
FIG. 10 depicts PCA results as a scores plot of the first three PCs (PC1 vs. PC2 vs. PC3) of the dielectric excitation response of FIG. 7.

PCA was also applied to analyze the dielectric excitation responses (e.g., impedance responses) of FIG. 7 to determine the ability of the gas sensor 10 to differentiate between the three analyte gases at a different single operating temperature. FIG. 10 depicts PCA results as a scores plot 180 of the first three PCs (PC1 vs. PC2 vs. PC3) of the dielectric excitation response of the gas sensing material 22 to seven preselected dielectric excitation frequencies when operated at the single operating temperature, wherein the single operation temperature in FIG. 8 corresponded to a heating element voltage of 5.0 V. More specifically, the scores plot 180 of FIG. 10 demonstrates differentiation between all three analyte gases. As such, FIG. 10 also unexpectedly demonstrates a strong correlation or proportional relationship between the dielectric excitations responses of the gas sensing material 22 and the respective concentrations of the three analyte gases, despite only a single operating temperature being used.

Thus, in the first experimental example, dielectric excitation responses of the sensor at a single operating temperature provided differentiation between all three tested gases, while resistance responses of the sensor at a two operating temperatures did not differentiate between two out of three gases, even when multiple operating temperatures were used. Again, performance of the gas sensor 10 under dielectric excitation provided a higher response dispersion (also known as sensor response dimensionality) even at a single operating temperature as compared to the response dispersion of the sensor with its resistance readout and operated at two temperatures. As shown in FIGS. 9 and 10, the gas sensor 10 under dielectric excitation and a single operation temperature demonstrated a three-dimensional response (3D dispersion) as compared to two-dimensional response (2D dispersion) of the gas sensor 10 with resistance responses of the sensor at a two operating temperatures.

Experimental Example 2

To further demonstrate the superior performance of the disclosed technique, experiments were performed to compare the ability of conventional resistance measurements to differentiate between different analyte gases in fluid samples relative to dielectric excitation measurements. For these experiments, all measurements were performed using an embodiment of a gas sensor 10 having dual gas sensing elements 12, each having a different MOS-based gas sensing material 22, both operated at a constant temperature. The measurements were performed by the measurement circuit 32 as either DC excitation responses (e.g., resistance measurements), or as dielectric excitation responses (e.g., impedance measurements) selected from the high-frequency shoulder region 106 of corresponding dielectric relaxation spectra 100 after dielectric excitation. FIGS. 11-14 correspond to a second example of operation of the gas sensor 10 when measured with its resistance response and under dielectric excitation.

Figure 11:
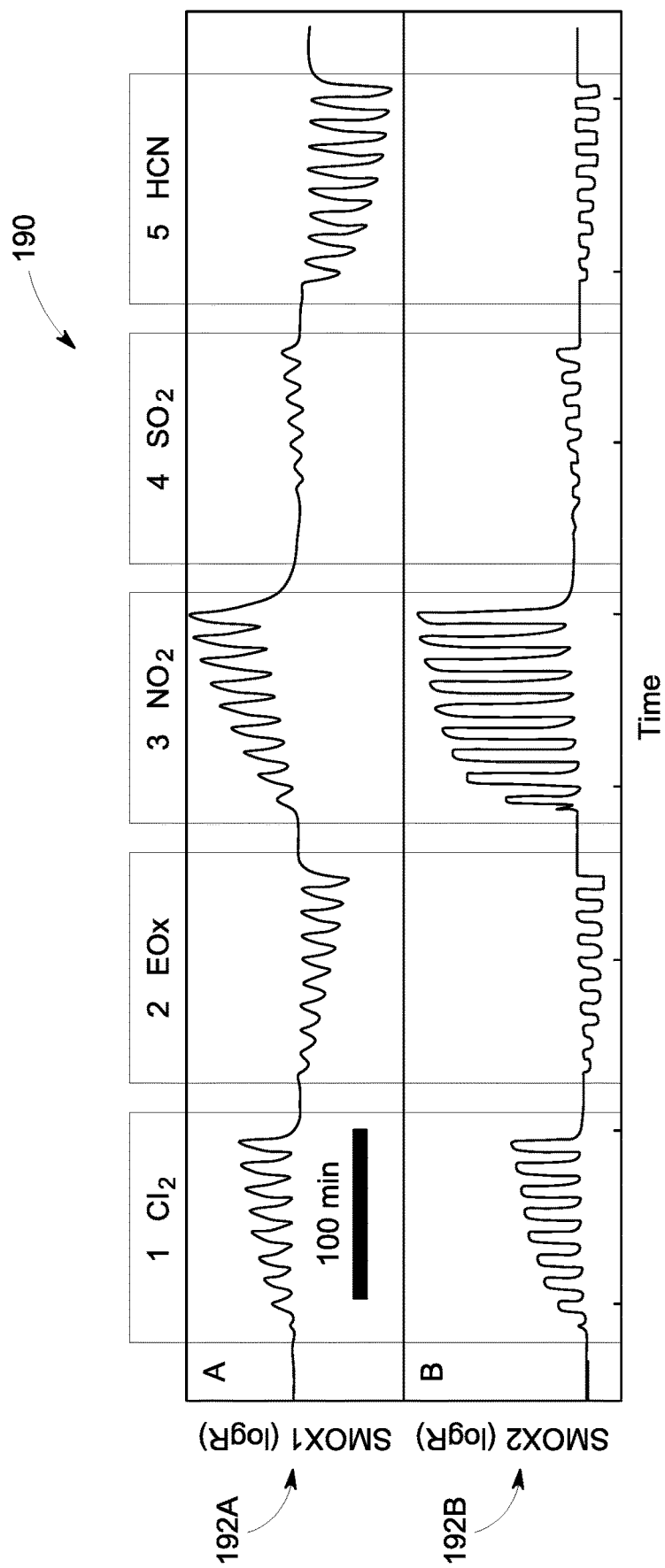
FIG. 11 is a set of graphs depicting example chemiresistor response patterns of two different gas sensing materials of a gas sensor operated at a constant temperature while exposed to five analyte gases, in accordance with aspects of the present technique.

The second experimental example demonstrates the advantage of dielectric excitation versus resistance readout of MOS-based gas sensing materials 22. More specifically, the second example demonstrates that dielectric excitation readout provides an advantage in improved multi-gas differentiation, as compared to resistance measurements with the same gas sensing materials in detection of diverse inorganic gases. For this experiment, the fluid sample 26 included a number of gases, including chlorine ($Cl_2$, gas 1), ethylene oxide (EOx, gas 2), nitrogen dioxide ($NO_2$, gas 3), sulfur dioxide ($SO_2$, gas 4), and hydrogen cyanide (HCN, gas 5). Each gas was presented to both gas sensing materials 22 of the gas sensor 10 with nine concentrations, equally spaced up to 75% of the maximum levels in the respective gas tanks. The concentrations in the respective gas tanks were 5 ppm, 10 ppm, 20 ppm, 20 ppm, and 25 ppm of $Cl_2$, EOx, $NO_2$, $SO_2$, and HCN, respectively. FIG. 11 is a set of graphs 190 illustrating responses of the gas sensor 10 having two different gas sensing materials 22 operated at a constant temperature with resistance (log scale) readout utilized for the multi-gas differentiation. Plot 192A of FIG. 11 illustrates that resistance response of the first gas sensing material 22 was strongest to gas 3, while responses to gases 1, 5, 2, and 4 were progressively decreasing. Additionally, the resistance responses to gases 1, 3, and 4 were in one direction, while responses to gases 2 and 5 were in the opposite direction. Plot 192B of FIG. 11 illustrates that resistance response of the second gas sensing material 22 was strongest to gas 3, while responses to gases 1, 2, 4, and 5 were progressively decreasing. Additionally, in FIG. 11, responses to gases 1, 3, and 4 were in one direction, while responses to gases 2 and 5 were in the opposite direction.

Figure 12:
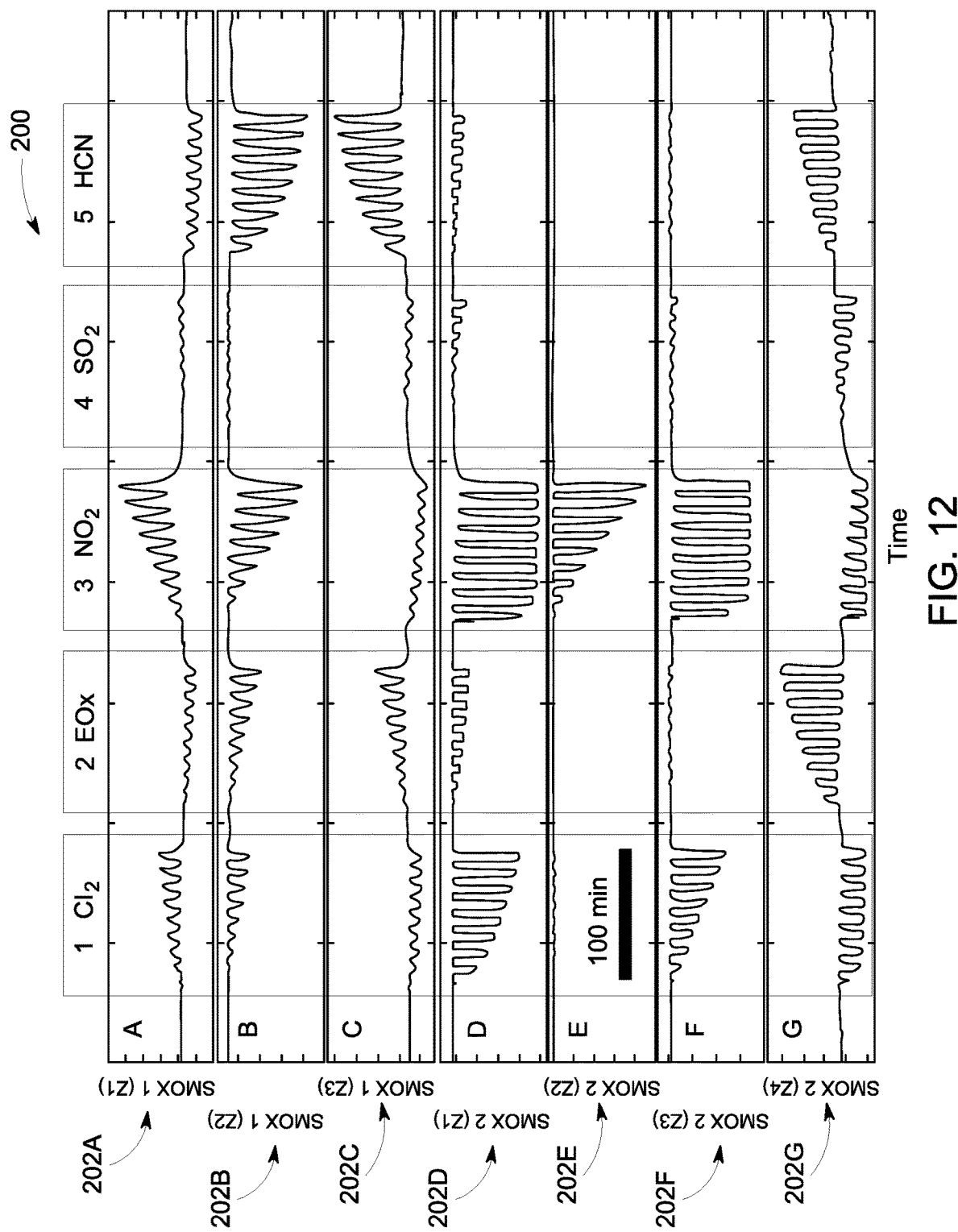
FIG. 12 is a set of graphs depicting example dielectric excitation response patterns of two different gas sensing materials of a gas sensor operated at a constant temperature while exposed to five analyte gases, in accordance with aspects of the present technique.

FIG. 12 is a set of graphs 200 illustrating responses of the gas sensor 10 having two different gas sensing materials 22 operated at a constant temperature with dielectric excitation readout (linear scale) utilized for the multi-gas differentiation. In comparison to FIG. 11, FIG. 12 depicts a substantial diversity in responses of the two gas sensing materials 22 of the gas sensor 10 under their dielectric excitation. For example, depending on the operation frequency, the strongest response can be either for gas 3 (plot 202A), gas (plots 202B and 202C), or gas 2 (plot 202G). The dielectric excitation responses to gases 1-5 can be similar to resistance response in opposite directions (plot 202A, 202C, 202G), or can be in the same direction (plots 202B and 202D). Such desired diversity of the responses at different frequencies enables an improved differentiation of gases as compared to resistance responses.

Figure 13:
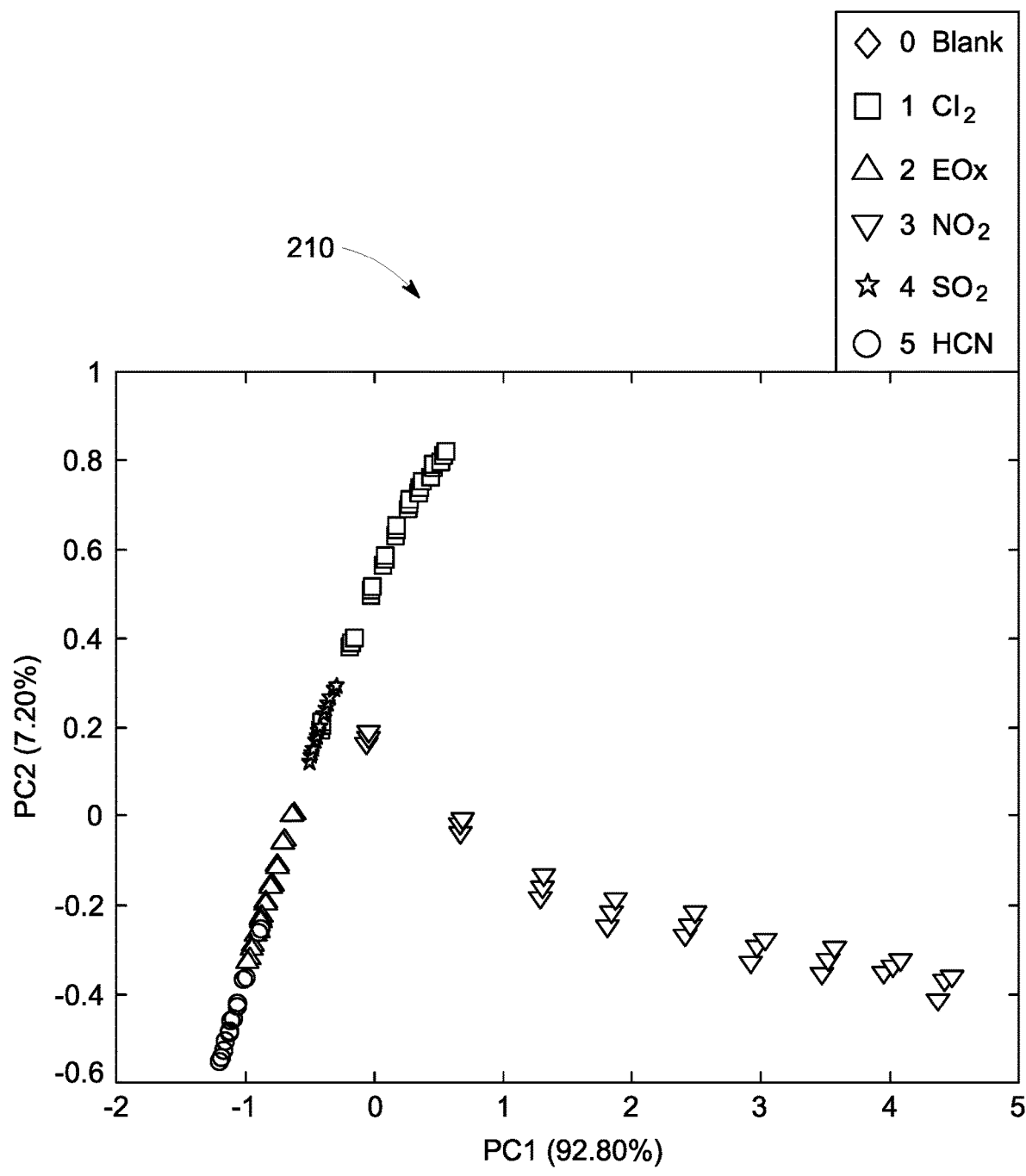
FIG. 13 depicts the results of PCA as a scores plot of the first two PCs (PC1 vs. PC2) of the resistance responses of FIG. 11, in accordance with aspects of the present technique.
Figure 14A:
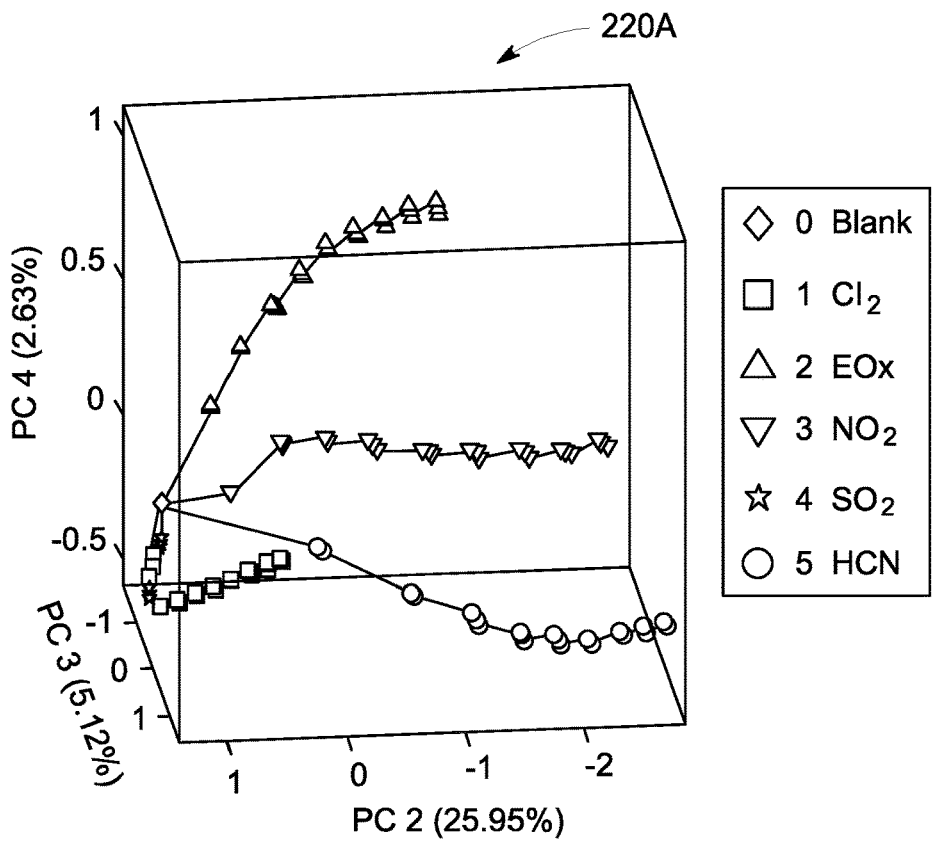
FIGS. 14A and 14B depict the results of PCA as scores plots of the three PCs (PC2 vs. PC3 vs. PC4) of the dielectric excitation responses of FIG. 12, in accordance with aspects of the present technique.
Figure 14B:
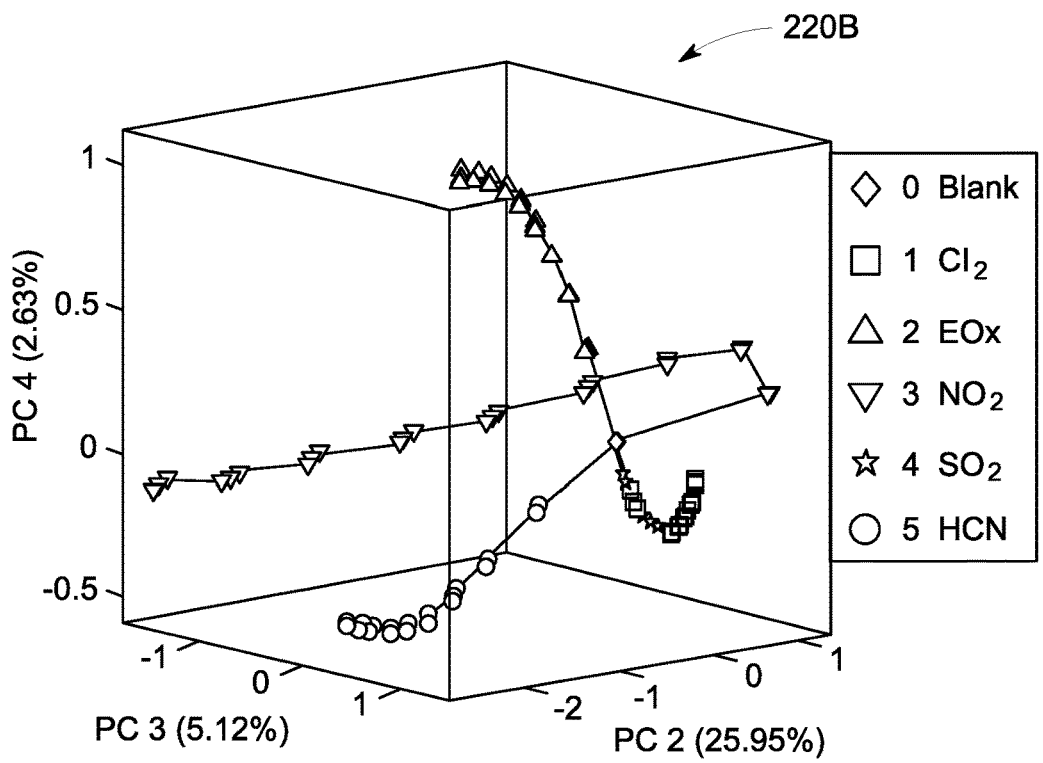

Results of PCA analysis of resistance responses of FIG. 11 and the dielectric excitation responses of FIG. 12 are presented in FIGS. 13 and 14, respectively. For this analysis, three data points per each concentration of the five gases and three points for the blank were extracted. FIG. 13 is the PCA scores plot 210 of resistance responses of FIG. 11, which illustrates an overlap between responses to gases 2 and 5, as well as some overlap between responses to gases 1 and 4. A clear differentiation is shown only between gas 3 and other gases 1, 2, 4, and 5. In contrast, FIGS. 14A and 14B are a set of PCA scores plots 220A and 220B of dielectric excitation responses of FIG. 12, which illustrates a clear differentiation between gas 2, gas 3, and gas 5, with limited overlap between responses to gases 1 and 4. Thus, dielectric excitation of the same number of gas sensing materials 22 enables enhanced differentiation between greater numbers of gases as compared to classic resistance readout. Such enhanced differentiation enables substantial benefits in terms of rejecting of interferents and reducing false alarms.

Experimental Example 3

To further demonstrate the superior performance of the disclosed technique, experiments were performed to compare the ability of conventional resistance measurements to differentiate between different analyte gases in fluid samples relative to dielectric excitation responses. For these experiments, all measurements were performed using an embodiment of a gas sensor 10 having dual gas sensing elements 12, each having a different MOS-based gas sensing material 22, both operated at a constant temperature. The measurements were performed by the measurement circuit 32 as either DC excitation responses (e.g., resistance measurements), or as dielectric excitation responses (e.g., impedance measurements) selected from the high-frequency shoulder region 106 of corresponding dielectric relaxation spectra 100 after dielectric excitation. FIGS. 15-20 correspond to a third example of operation of the gas sensor 10 when measured with its resistance response and under dielectric excitation.

Figure 15:
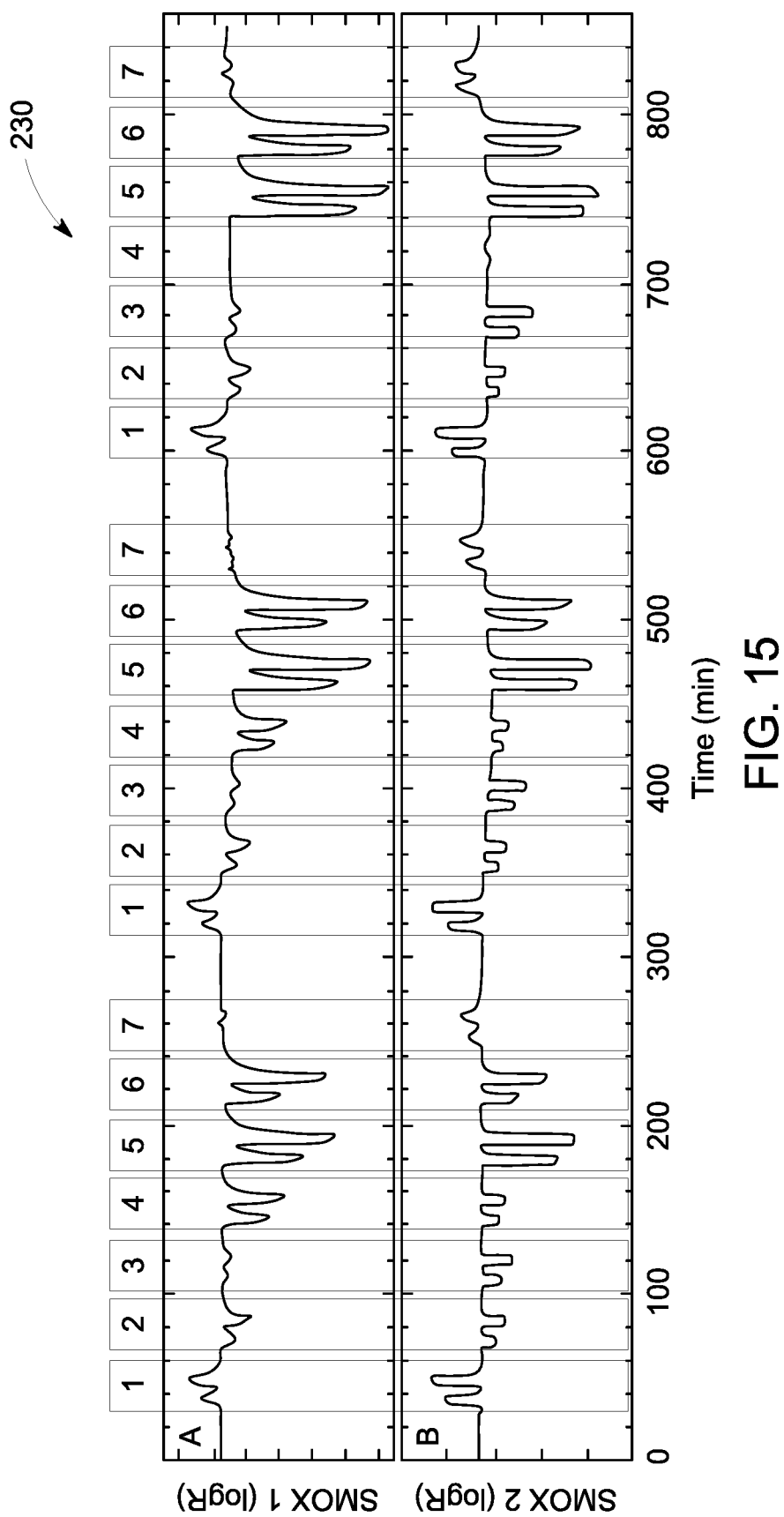
FIG. 15 is a set of graphs depicting examples of chemiresistor response patterns of two different gas sensing materials of a gas sensor operated at a constant temperature while exposed over three cycles with the same two levels of analytes and increasing levels of interferents, in accordance with aspects of the present technique.
Figure 16:
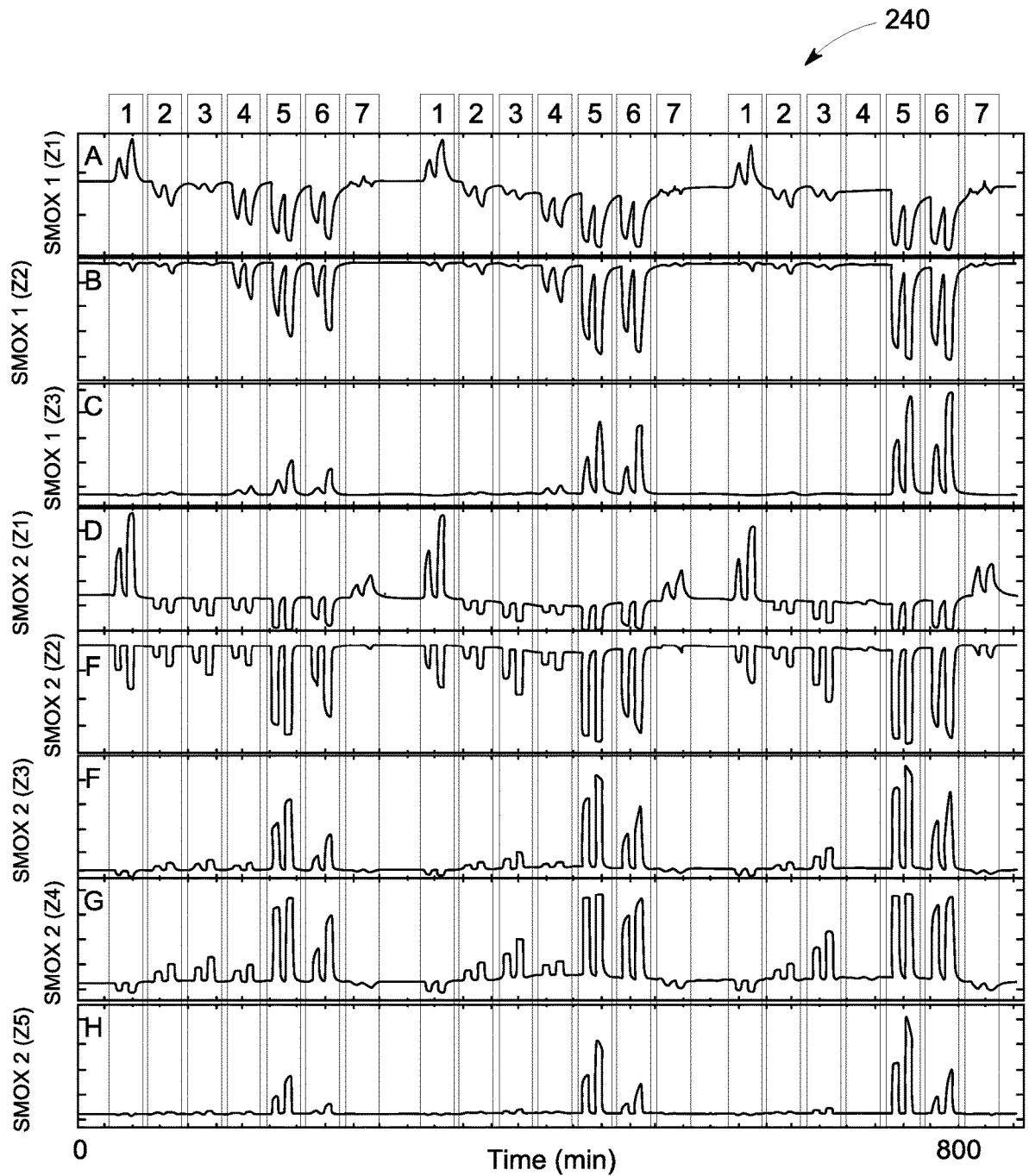
FIG. 16 is a set of graphs depicting examples of dielectric excitation response patterns for the embodiment of the gas sensor having two different gas sensing materials over three cycles with the same two levels of analytes and increasing levels of interferents, in accordance with aspects of the present technique.

In the third experimental example, using the two gas sensing materials 22 of the gas sensor 10 operated at a constant temperature, effects of increasing levels of interferents on the ability to differentiate analyte gases of interest were studied. The analyte gases included chlorine ($Cl_2$, gas 1), ethylene oxide (EOx, gas 2) and hydrogen cyanide (HCN, gas 4), while the interferents included diesel exhaust (gas 3), isopropyl alcohol (IPA, gas toluene (gas 6), and humidity (gas 7). These gases were presented to gas sensing materials 22 of the gas sensors 10 with their increasing concentrations. It may be noted that the analyte gases were selected to evaluate effects of interferents on analytes that tend to provide relatively strong sensor responses (e.g., to $Cl_2$), as well as analytes that tend to provide relatively weaker sensor responses (e.g., to EOx and HCN). Responses of the two gas sensing materials 22 were collected over three cycles with the same two levels of analytes (gases 1, 2, and 4) and increasing levels of interferents (gases 3, 5, 6, and 7). The graphs 230 of FIG. 15 depict the resistance responses of the two gas sensing materials 22, while the graphs 240 of FIG. 16 depict the dielectric excitation responses.

Figure 17:
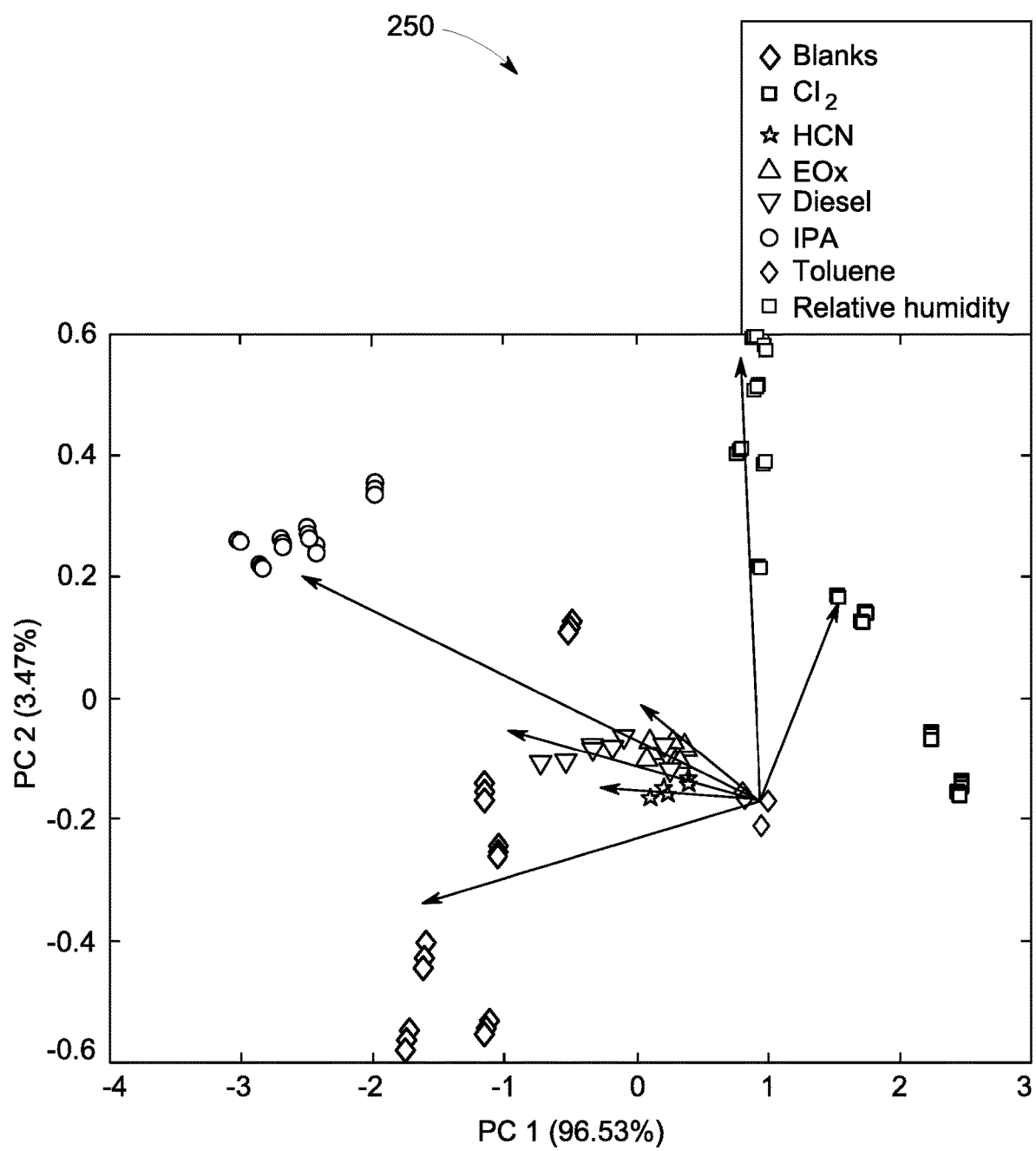
FIG. 17 depicts the results of PCA as a scores plot of the two PCs (PC1 vs. PC2) of the resistance responses of FIG. 15, in accordance with aspects of the present technique.
Figure 18:
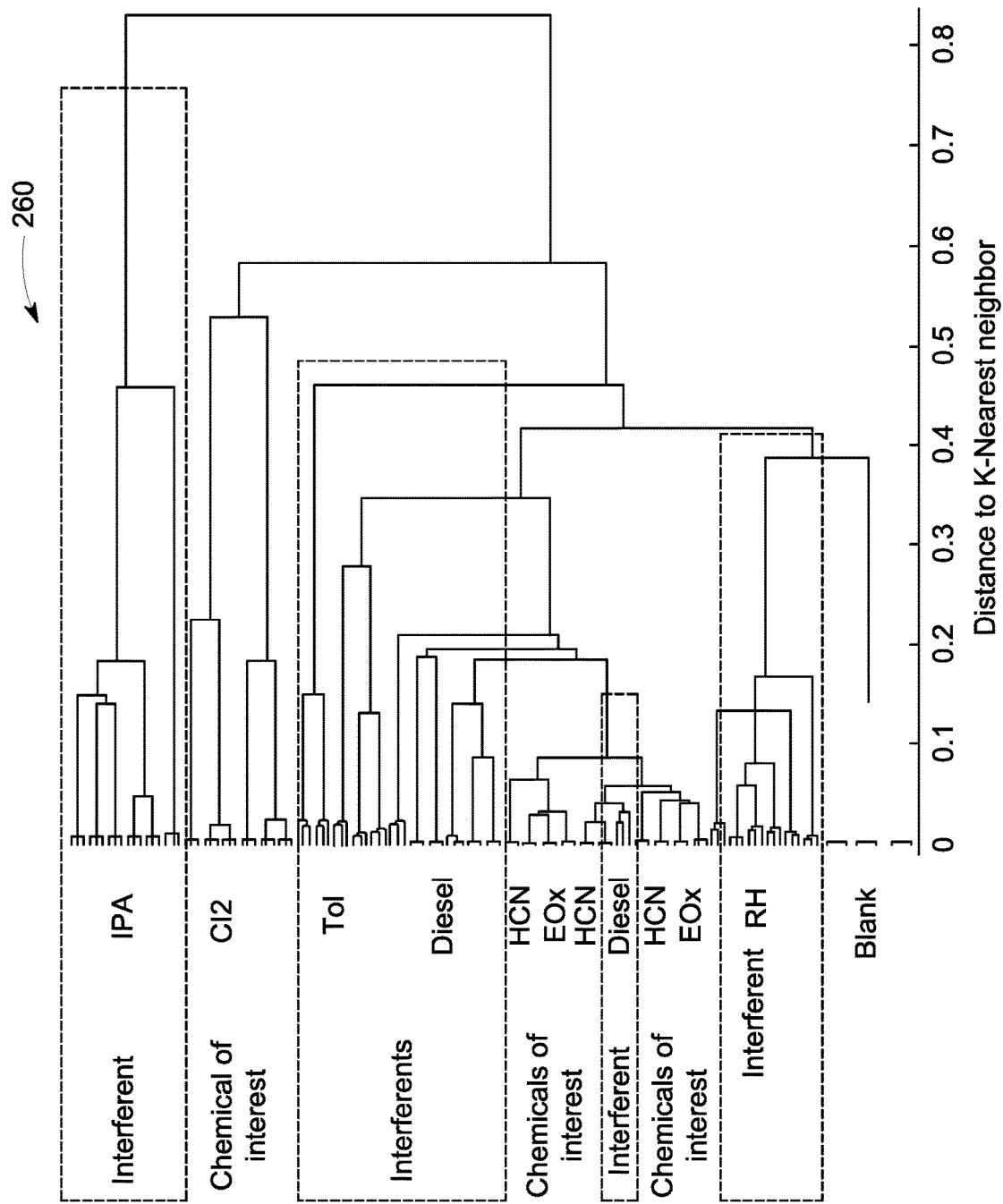
FIG. 18 depicts the results of hierarchical cluster analysis (HCA) as an HCA dendrogram plot of the resistance responses of FIG. 15, in accordance with aspects of the present technique.

To assess the ability of a limited number of gas sensing materials 22 (e.g., two gas sensing materials 22) in the embodiment of the gas sensor 10 to differentiate between many gases, the resistance responses of these two gas sensing materials 22 were analyzed using principal component analysis (PCA) and hierarchical cluster analysis (HCA) algorithms. As illustrated in FIG. 17, the PCA scores plot 250 includes both principal components (PCs) corresponding to responses of the two gas sensing materials 22, which describes all (i.e., 100%) of the variation in the data set from the two gas sensing materials 22 with their single-output readouts as its 2D dispersion. The 2D dispersion is mathematically the highest dispersion that can be achieved by using two gas sensors with single-output readouts. As illustrated in FIG. 17, the PCA scores plot 250 from resistance responses of the two gas sensing materials 22 depicts that IPA, toluene, RH, and $Cl_2$ were well-differentiated, while HCN, EOx, and diesel undesirably demonstrated strong overlap. As illustrated by FIG. 18, the HCA plot 260 from resistance responses of the two gas sensing materials 22 demonstrated inability to differentiate between some diesel responses and all HCN and EOx responses and inability to differentiate between HCN and EOx responses. Thus, embodiments of the gas sensor 10 having two gas sensing materials 22 with single-output resistance responses did not differentiate between HCN, EOx and diesel.

Figure 19:
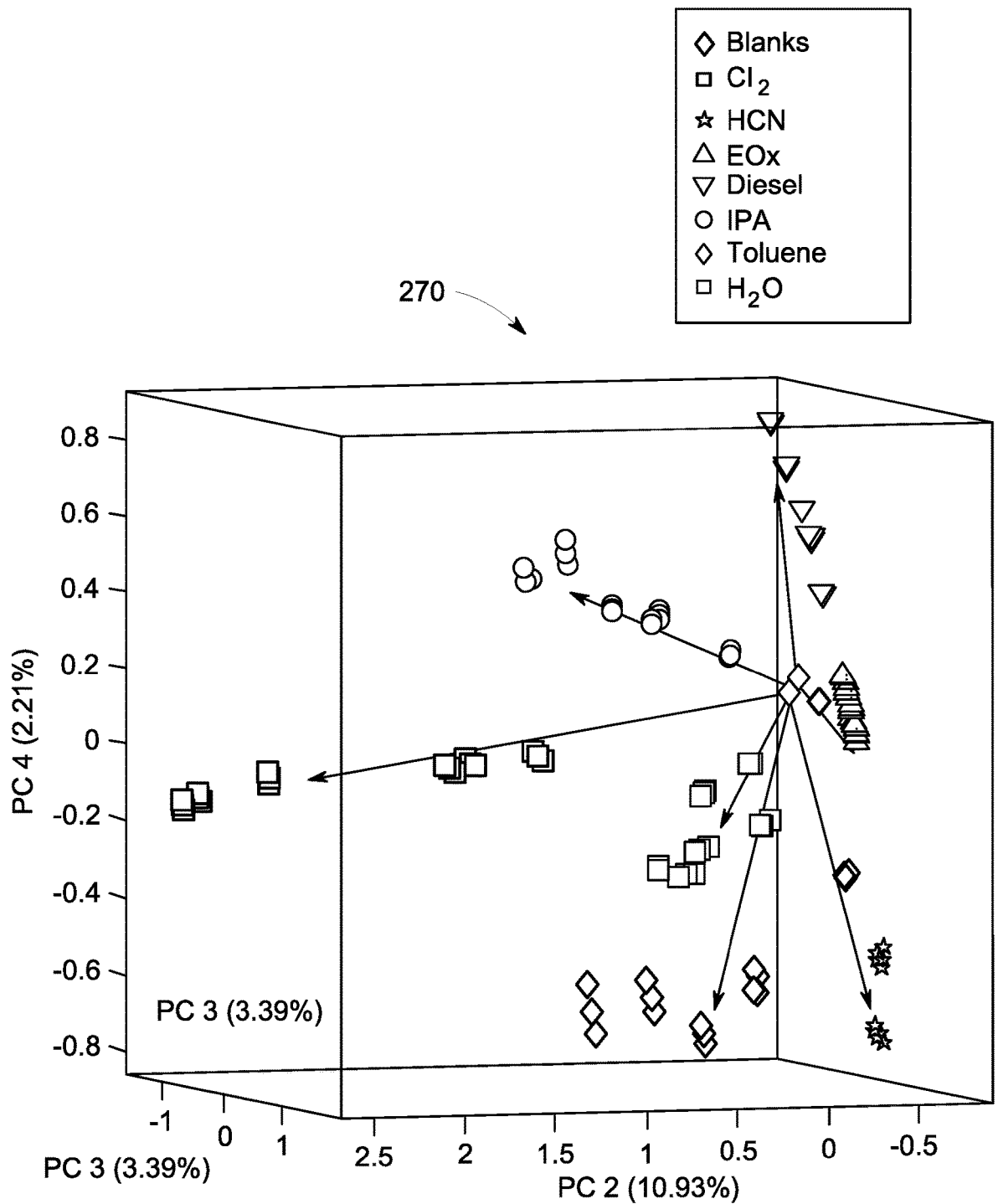
FIG. 19 depicts the results of PCA as a scores plot of three PCs (PC2 vs. PC3 vs. PC4) of the dielectric excitation responses of FIG. 16, in accordance with aspects of the present technique.
Figure 20:
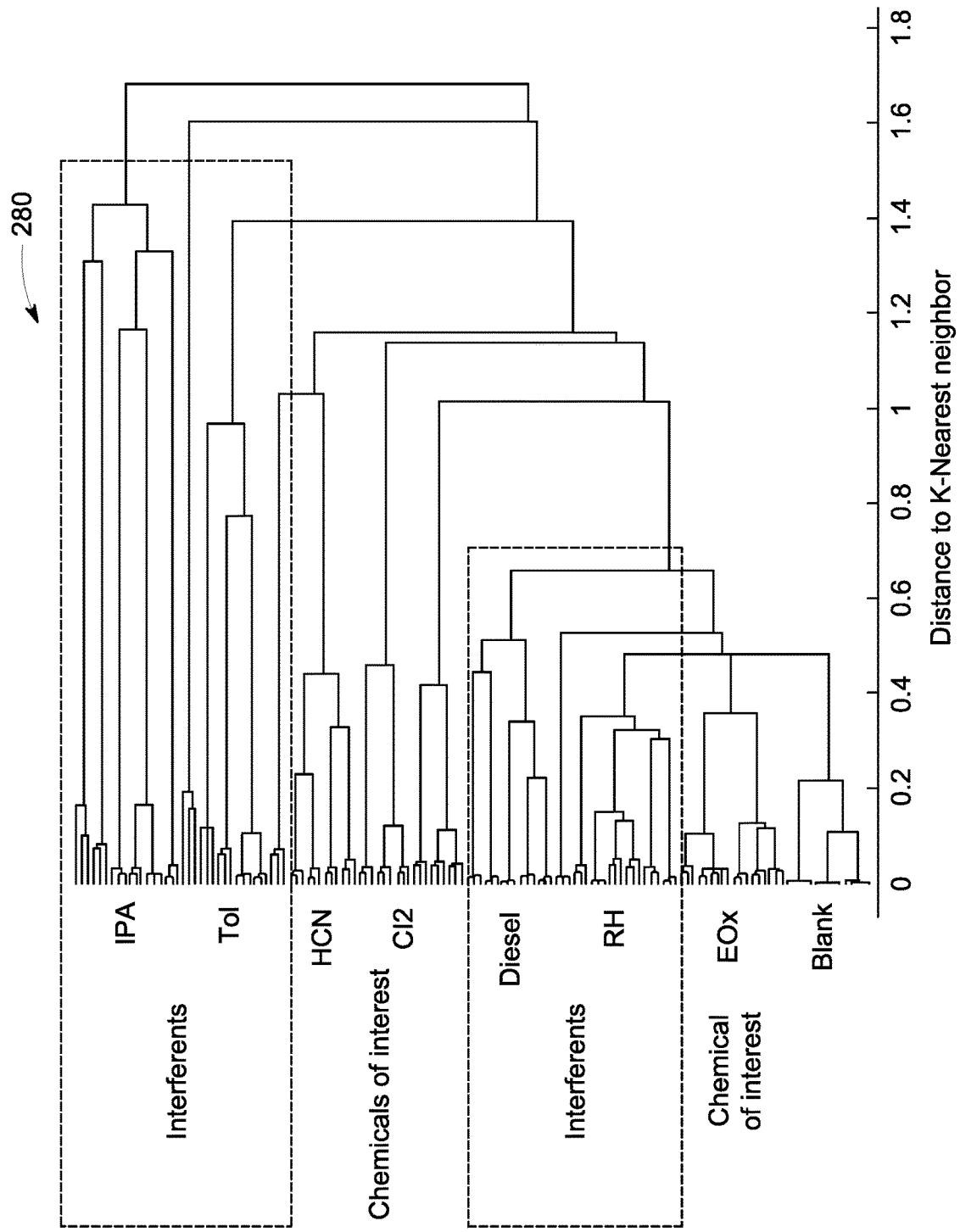
FIG. 20 depicts the results of HCA as an HCA dendrogram plot of the dielectric excitation responses of FIG. 16, in accordance with aspects of the present technique.

In comparison, results of PCA and HCA analysis of dielectric excitation responses of the gas sensor 10 having the two gas sensing materials 22 are presented in FIGS. 19 and 20, respectively. As illustrated in FIG. 19, the PCA scores plot 270 is PC2 versus PC3 versus PC4, which highlights a 4D dispersion of the sensor response under dielectric excitation, while, at most, only a 2D dispersion of the sensor response can be achieved with single-output resistance readout, as depicted in FIG. 17. The PCA scores plot 270 from dielectric excitation responses of the two gas sensing materials 22 depicts that all gases, including diesel exhaust gas, were well-differentiated. As illustrated in FIG. the HCA plot 280 from dielectric excitation responses of the two gas sensing materials 22 demonstrated clear clusters of responses to analyte gases HCN, $Cl_2$, and EOx, as well as two clusters of interferents, including IPA and toluene (cluster 1) and diesel exhaust and humidity (cluster 2). Thus, the embodiment of the gas sensor 10 having the two gas sensing materials 22 with their multi-output dielectric excitation responses well-differentiate all tested gases, including differentiation of diesel exhaust from other gases.

Figure 21:
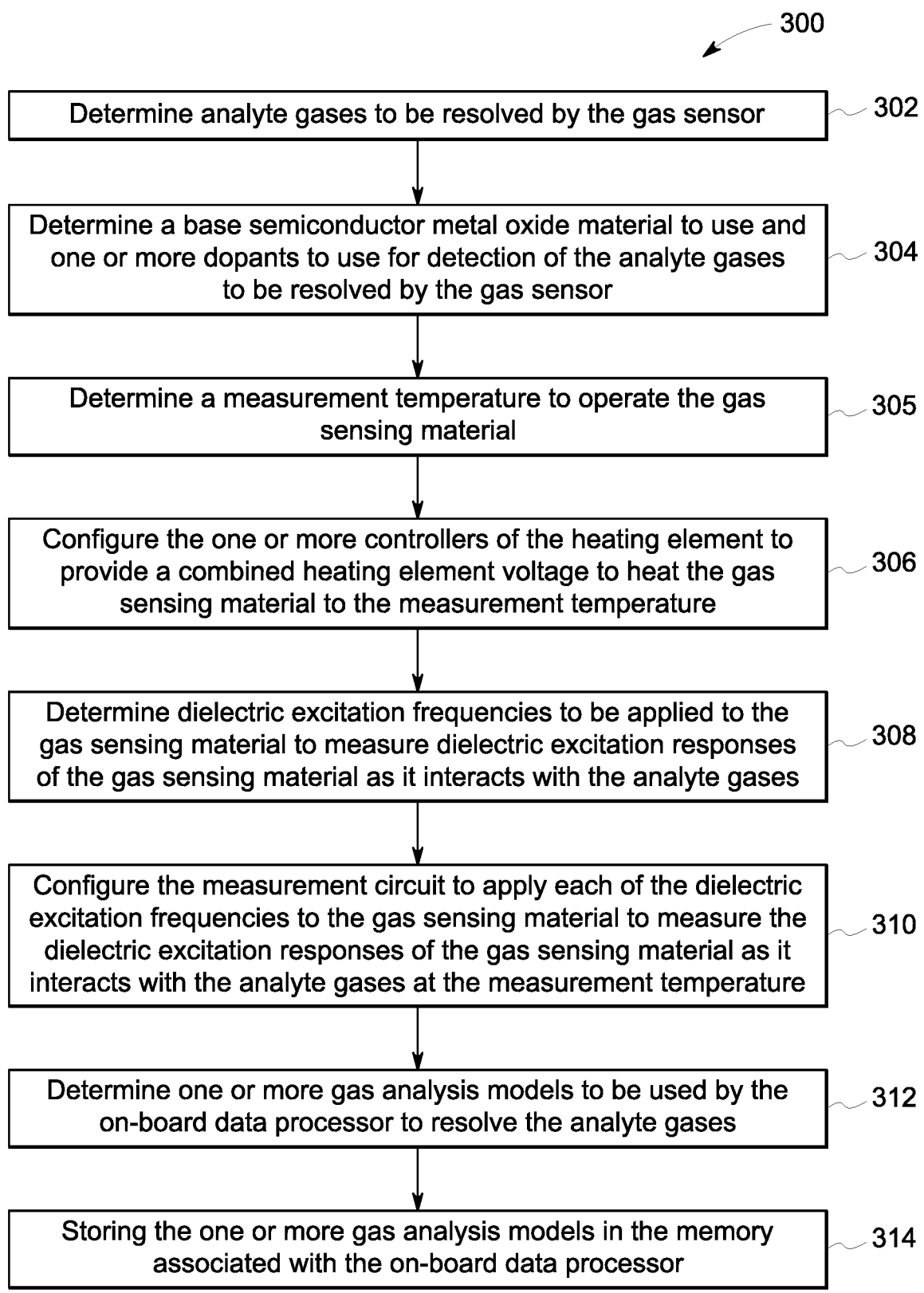
FIG. 21 is a flow diagram illustrating an embodiment of a process whereby the gas sensor can be manufactured and configured for use to differentiate particular gas analytes during multi-gas analysis, in accordance with aspects of the present technique.

With the foregoing in mind, FIG. 21 is a flow diagram illustrating an embodiment of a process 300 whereby the gas sensor 10 can be manufactured and configured to differentiate particular gas analytes during multi-gas analysis. For the illustrated embodiment, the process 300 begins with the designer determining (block 302) a plurality of analyte gases to be differentiated by the gas sensor 10. Based on the analyte gases to be differentiated by the gas sensor 10, the designer determines (block 304) a base semiconducting metal oxide material 22 to use and one or more dopants to use for detection of analyte gases to be differentiated by the gas sensor. The designer also determines (block 305) an operating temperature to operate the gas sensing material 22 of the gas sensor 10, and configures (block 306) the first controller 28A of the heating element 24 and the second controller 28B of the heating element 24 to provide a suitable combined heating element voltage to heat the gas sensing material 22 to the operating temperature. Based on the analyte gases to be differentiated by the gas sensor 10, the designer also determines (block 308) dielectric excitation frequencies to be applied to the gas sensing material 22 to measure dielectric excitation responses of the gas sensing material 22 as it interacts with the plurality of analyte gases, and configures (block 310) the measurement circuit 32 to apply each of the dielectric excitation frequencies to the gas sensing material 22 to measure the dielectric excitation responses of the gas sensing material 22 as it interacts with the analyte gases at the operating temperature. For embodiments in which the gas sensor 10 includes the on-board data processor 36, the process 300 may include the designer determining (block 312) one or more gas analysis models 40 to be used by the on-board data processor 36 to differentiate the analyte gases, and storing (block 314) the one or more gas analysis models 40 in the memory 38 associated with the on-board data processor 36. In certain embodiments, determining the gas analysis models 40 may include generating at least one an equation (and/or determining corresponding coefficient values of an equation) that relates experimentally measured dielectric excitation responses of the gas sensing material 22 at the constant operating temperature to each of the analyte gases and certain classifications of the analyte gases, or certain concentrations of the analyte gases, or any combination thereof. In certain embodiments, plurality of gases can include at least one analyte gas and at least one interference gas. In certain embodiments, multivariate data processing principles can be applied to perform classification/cluster analysis and quantitation of gases.

In certain embodiments, in block 304, the desired operating temperature of the gas sensor 10 may be experimentally determined. For example, the gas sensing material 22 of the gas sensor 10 may be exposed to a sensing environment (e.g., a controlled, variable fluid sample) to collect excitation responses while heating the gas sensing material 22 to different operating temperatures. At each of the different operating temperatures, a first sequence of increasing concentrations of a first analyte gas is introduced into the sensing environment, while the measurement circuit 32 applies at least one of the plurality of dielectric excitation frequencies to the gas sensing material 22 to measure a first set of dielectric excitation responses of the gas sensing material 22 to the first sequence of increasing concentrations of the first analyte gas at the particular temperature. Additionally, at each of the different temperatures, a second sequence of increasing concentrations of a second analyte gas is introduced into the sensing environment while applying at least one of the plurality of dielectric excitation frequencies to the gas sensing material 22 to measure a second set of dielectric excitation responses of the gas sensing material 22 to the second sequence of increasing concentrations of the second analyte gas at the particular temperature. Subsequently, the first set of dielectric excitation responses at each of the different temperatures, and the second set of dielectric excitation responses at each of the different temperatures, are analyzed (e.g., using PCA, as discussed above) to determine the at least one operating temperature to operate the gas sensing material 22 of the gas sensor 10 when detecting the first and second analytes in a fluid sample. For example, based on the PCA or any other multivariate analysis algorithm, a desired constant operating temperature may be identified at which the first set of dielectric excitation responses is correlated with or proportional to a concentration of the first analyte gas, and at which the second set of dielectric excitation responses of the gas sensing material 22 is correlated with or proportional to a concentration of the second analyte gas. It may be appreciated that this experimental determination of the operating temperature may be expanded to include more than two analyte gases, such as three, four, or five or more analyte gases.

In certain embodiments, in block 308, the plurality of dielectric excitation frequencies to be used by the measurement circuit 32 may be experimentally determined. For example, the gas sensing material 22 of the gas sensor 10 may be exposed to the sensing environment while heating the gas sensing material to a desired operating temperature. A first sequence of increasing concentrations of a first analyte gas is then introduced into the sensing environment. For each of the concentrations of the first analyte gas of the first sequence, the measurement circuit 32 applies a first set of dielectric excitation frequencies to the gas sensing material 22 to measure a first set of dielectric excitation responses of the gas sensing material 22 to the first sequence of increasing concentrations of the first analyte gas. A second sequence of increasing concentrations of a second analyte gas is introduced into the sensing environment. For each of the concentrations of the second analyte gas of the second sequence, the measurement circuit 32 applies a second set of dielectric excitation frequencies to the gas sensing material 22 to measure a second set of dielectric excitation responses of the gas sensing material 22 to the second sequence of increasing concentrations of the second analyte gas. Then, the first set of dielectric excitation responses at each of the different concentrations of the first analyte gas, and the second set of dielectric excitation responses at each of the different concentrations of the second analyte gas, are analyzed (e.g., using PCA, as discussed above) to determine, from the first set of dielectric excitation frequencies and the second set of dielectric excitation frequencies, the plurality of dielectric excitation frequencies to operate the gas sensing material 22 during multi-gas sensing in a fluid sample. For example, based on the PCA, at least two dielectric excitation frequencies may be identified at which the corresponding dielectric excitation responses are correlated with or proportional to the concentration of the first analyte gas, the concentration of the second analyte gas, or a combination thereof.

Technical effects of this disclosure include enabling multi-gas sensing at a constant operating temperature. Using the disclosed techniques, a MOS-based gas sensor can be designed, manufactured, and used to differentiate a plurality of gases in a fluid sample at a single operating temperature. Maintaining the gas sensing element at the constant operating temperature offers a number of advantages in terms of improved efficiency, improved electrical measurements, and improved operational lifetime of the gas sensor. By measuring and analyzing dielectric excitation responses of the gas sensing material at the constant operating temperature, the gas sensor unexpectedly provides superior multi-gas selectivity compared to other gas sensors and other gas sensing methods that rely on multiple resistance measurements performed at several different operating temperatures.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A gas sensor system for multi-gas analysis of a fluid sample, comprising:
a gas sensing element configured to contact the fluid sample;
a heating element coupled to the gas sensing element and configured to heat the gas sensing element;
a first heating element controller operatively coupled to the heating element and configured to provide a predetermined constant voltage to the heating element while the gas sensing element contacts the fluid sample;
a second heating element controller operatively coupled to the heating element and configured to provide an additional adjustable voltage to the heating element while the gas sensing element contacts the fluid sample, wherein a combination of the predetermined constant voltage and the additional adjustable voltage is used to heat the heating element to a constant temperature; and
a measurement circuit operatively coupled to the gas sensing element and configured to provide a dielectric excitation to, and to measure dielectric excitation responses of, the gas sensing element while the gas sensing element is heated to the constant temperature and contacts the fluid sample, wherein the dielectric excitation responses are used to provide an enhanced differentiation between at least two gases in the fluid sample.

2. The gas sensor system of claim 1, comprising:
a second gas sensing element configured to contact the fluid sample; and
a second heating element coupled to the second gas sensing element and configured to heat the second gas sensing element,
wherein the first heating element controller and the second heating element controller are operatively coupled to the second heating element and configured to control the second heating element to heat the second gas sensing element to the constant temperature while the second gas sensing element contacts the fluid sample, wherein the measurement circuit is operatively coupled to the second gas sensing element and configured to provide a second dielectric excitation to, and to measure second dielectric excitation responses of, the second gas sensing element while the second gas sensing element is heated to the constant temperature and contacts the fluid sample, wherein the second dielectric excitation responses are used to provide the enhanced differentiation between the at least two gases in the fluid sample.

3. The gas sensor system of claim 1, comprising:
an on-board data processor communicatively coupled to the measurement circuit and configured to receive, from the measurement circuit, the dielectric excitation responses of the gas sensing element at the constant temperature while the gas sensing element contacts the fluid sample, and to select at least two of the dielectric excitation responses of the gas sensing element at the constant temperature to differentiate the at least two gases in the fluid sample.

4. The gas sensor system of claim 3, wherein the at least two of the dielectric excitation responses are impedance responses of the gas sensing element at the constant temperature.

5. The gas sensor system of claim 3, wherein the on-board data processor is configured to differentiate the at least two gases by determining respective classifications, respective concentrations, or a combination thereof, of the at least two gases in the fluid sample based on the at least two of the dielectric excitation responses of the gas sensing element at the constant temperature.

6. The gas sensor system of claim 1, wherein the constant temperature is between 80° C. and 600° C.

7. The gas sensor system of claim 1, wherein the constant temperature varies by less than 20% while the gas sensing element contacts the fluid sample.

8. The gas sensor system of claim 1, wherein the second heating element controller is configured to adjust the additional adjustable voltage based on a temperature of the gas sensing element measured by a temperature sensor.

9. A method of operating a gas sensor for multi-gas analysis of a fluid sample, comprising:
exposing a gas sensing material of the gas sensor to the fluid sample;
providing, via a first heating element controller, a predetermined constant voltage to a heating element coupled to the gas sensing material and configured to heat the gas sensing material;
providing, via a second heating element controller, an additional adjustable voltage to the heating element;

adjusting, via the second heating element controller, the additional adjustable voltage provided to the heating element to heat the gas sensing material to a constant temperature;

measuring, via a measurement circuit of the gas sensor, dielectric excitation responses of the gas sensing material while the gas sensing material is heated to the constant temperature and exposed to the fluid sample;

receiving, via an on-board data processor of the gas sensor, the dielectric excitation responses of the gas sensing material measured at the constant temperature; and differentiating, via the on-board data processor, at least two gases in the fluid sample based on at least a portion of the dielectric excitation responses.

10. The method of claim 9, comprising:
exposing a second gas sensing material of the gas sensor to the fluid sample;
controlling, via the first heating element controller and the second heating element controller, a second heating element of the gas sensor to heat the second gas sensing material to the constant temperature;
measuring, via the measurement circuit of the gas sensor, second dielectric excitation responses of the second gas sensing material while the second gas sensing material is heated to the constant temperature and exposed to the fluid sample;
receiving, via the on-board data processor of the gas sensor, the second dielectric excitation responses of the second gas sensing material at the constant temperature; and
differentiating, via the on-board data processor, the at least two gases in the fluid sample based on at least a portion of the second dielectric excitation responses.

11. The method of claim 9, wherein adjusting the additional adjustable voltage provided to the heating element comprises:
measuring, via a temperature sensor coupled to the gas sensing material and communicatively coupled to the second heating element controller, an initial temperature of the gas sensing material in response to the predetermined constant voltage provided to the heating element while exposed to the fluid sample;
determining, via the second heating element controller, a difference between the initial temperature and the constant temperature; and
determining, via the second heating element controller, the additional adjustable voltage to be provided by the second heating element controller to heat the gas sensing material to the constant temperature.

12. The method of claim 9, wherein adjusting the additional adjustable voltage provided to the heating element comprises:
measuring resistance of the heating element that is correlated to a temperature of the heating element;
determining, via the second heating element controller of the gas sensor, a difference between an initial temperature and the constant temperature; and
determining, via the second heating element controller, the additional adjustable voltage to be provided by the second heating element controller to heat the gas sensing material to the constant temperature.

13. The method of claim 9, wherein measuring comprises:
measuring, via the measurement circuit, two or more dielectric excitation responses of the gas sensing material at two or more excitation frequencies that are correlated with respective concentrations and respective classifications of two or more gases in the fluid sample.

14. The method of claim 13, wherein differentiating the at least two gases in the fluid sample comprises:
determining, via the on-board data processor, the respective concentrations of the two or more gases in the fluid sample based on the two or more dielectric excitation responses and a stored quantitation model that correlates a plurality of dielectric excitation responses measured at different excitation frequencies to concentrations of different gases.

15. The method of claim 14, wherein differentiating the at least two gases in the fluid sample comprises:
determining, via the on-board data processor, the respective classifications of the two or more gases in the fluid sample based on the two or more dielectric excitation responses and a stored classification model that correlates another plurality of dielectric excitation responses measured at the different excitation frequencies to classifications of the different gases.

16. A method of operating a gas sensor for multi-gas analysis, comprising:
determining a plurality of analyte gases to be differentiated by the gas sensor;
determining a semiconductor gas sensing material composition;
determining an operating temperature to operate the gas sensing material of the gas sensor at which the gas sensing material reversibly interacts with each of the plurality of analyte gases;
configuring a first heating element controller and a second heating element controller of the gas sensor to provide a combined voltage to a heating element of the gas sensor to heat the gas sensing material to the operating temperature by:
providing, via the first heating element controller, a predetermined constant voltage to the heating element coupled to the gas sensing material and configured to heat the gas sensing material;
providing, via the second heating element controller, an additional adjustable voltage to the heating element; and
adjusting, via the second heating element controller, the additional adjustable voltage so that the combined voltage of the predetermined constant voltage and the additional adjustable voltage heat the gas sensing material to the operating temperature;
determining a plurality of dielectric excitation frequencies to be applied to the gas sensing material to measure dielectric excitation responses of the gas sensing material as the gas sensing material interacts with the plurality of analyte gases; and
configuring a measurement circuit of the gas sensor to apply each of the plurality of dielectric excitation frequencies to the gas sensing material to measure the dielectric excitation responses of the gas sensing material as the gas sensing material interacts with the plurality of analyte gases at the operating temperature.

17. The method of claim 16, wherein the second heating element controller is configured to adjust the additional adjustable voltage based on a temperature of the gas sensing material measured by a temperature sensor.

\* \* \* \* \*